United States Patent
Richter et al.

(10) Patent No.: US 10,342,570 B2
(45) Date of Patent: Jul. 9, 2019

(54) DEVICE FOR TRAVERSING VESSEL OCCLUSIONS AND METHOD OF USE

(71) Applicant: MEDINOL LTD., Tel Aviv (IL)

(72) Inventors: Jacob Richter, Arsuf (IL); Amir Panksy, Atlit (IL)

(73) Assignee: Medinol Ltd., Tel Aviv (IL)

( * ) Notice: Subject to any disclaimer, the term of this patent is extended or adjusted under 35 U.S.C. 154(b) by 24 days.

(21) Appl. No.: 14/170,867

(22) Filed: Feb. 3, 2014

(65) Prior Publication Data

US 2015/0216550 A1    Aug. 6, 2015

(51) Int. Cl.
   *A61B 17/22* (2006.01)
   *A61B 17/3207* (2006.01)
   *A61B 17/32* (2006.01)

(52) U.S. Cl.
   CPC .............. *A61B 17/3207* (2013.01); *A61B 17/320068* (2013.01); *A61B 2017/22042* (2013.01);
   (Continued)

(58) Field of Classification Search
   CPC .............. A61B 17/32075; A61B 17/22; A61B 17/22012; A61B 17/22004;
   (Continued)

(56) References Cited

U.S. PATENT DOCUMENTS 3,618,613 A    11/1971 Schulte
3,981,297 A    9/1976 Dunn et al.
(Continued)

FOREIGN PATENT DOCUMENTS

CA    2703926    5/2014
CN    101926667 A    12/2010
(Continued)

OTHER PUBLICATIONS

Spring. (n.d.) Random House Kerneman Webster's College Dictionary. (2010). Retrieved Jun. 25, 2016 from http://www.thefreedictionary.com/spring.*
(Continued)

*Primary Examiner* — Elizabeth Houston
*Assistant Examiner* — Kankindi Rwego
(74) *Attorney, Agent, or Firm* — Cadwalader, Wickersham & Taft LLP

(57) ABSTRACT

An apparatus, system and method for re-canalization or opening a passage through an occlusion in a blood vessel is provided. The apparatus and method, which are appropriate for cardiovascular and peripheral vessels, use a pulling member and a spring member, for example a compression spring, to oscillate a drilling component. The drilling component at the distal end of the catheter tip has combined longitudinal stiffness for penetrating a total or partial occlusion and high axial (lateral) flexibility to improve deliverability and crossability of a catheter through a partially occluded vessel or a tortuous vessel, and may taper distally. The system of the invention includes the apparatus and a control unit to permit adjustment of the frequency or amplitude of oscillation of the drilling component. Also provided is a method for oscillating a drilling component using a pulling member and a spring member and a method of traversing an occlusion.

26 Claims, 5 Drawing Sheets

(52) U.S. Cl.
CPC ............... *A61B 2017/22044* (2013.01); *A61B 2017/22094* (2013.01)

(58) Field of Classification Search
CPC ........... A61B 2017/22011; A61B 2017/22042; A61B 2017/22044; A61B 2017/22045; A61B 2017/22094; A61B 17/320068; A61B 17/3207; A61B 2017/32072; A61B 2017/32073; A61B 17/32002; A61B 17/320758; A61B 2017/22077; A61B 17/320028; A61B 17/320032; A61B 17/320056; A61B 17/32072; A61B 17/3273; A61M 25/008; A61M 25/0082; A61M 25/0067; A61M 25/0074; A61M 25/0113; A61M 25/0194; A61M 2025/0084; A61M 2025/0085; A61M 2025/0086; A61M 2025/0087; A61M 2025/0089; A61M 2025/009; A61M 2025/0091; A61M 2025/0092; A61M 2025/0093; A61M 2025/0095; A61M 2025/0096; A61M 2025/0197; A61M 2025/09091; A61F 9/00745
USPC ........................... 606/159, 194; 604/22, 523
See application file for complete search history.

(56) References Cited

U.S. PATENT DOCUMENTS

| | | | |
|---|---|---|---|
| 4,044,765 | A | 8/1977 | Kline |
| 4,215,703 | A * | 8/1980 | Willson .......... A61M 25/09033 600/585 |
| 4,616,652 | A | 10/1986 | Simpson |
| 4,665,604 | A | 5/1987 | Dubowik |
| 4,705,511 | A | 11/1987 | Kocak |
| 4,734,093 | A | 3/1988 | Bonello et al. |
| 4,793,350 | A | 12/1988 | Mar et al. |
| 4,846,174 | A | 7/1989 | Willard et al. |
| 4,985,022 | A | 1/1991 | Fearnot et al. |
| 5,112,304 | A | 5/1992 | Barlow et al. |
| 5,195,954 | A * | 3/1993 | Schnepp-Pesch ........................... A61B 17/320758 604/22 |
| 5,234,451 | A | 8/1993 | Osypka |
| 5,243,997 | A | 9/1993 | Uflacker et al. |
| 5,256,145 | A | 10/1993 | Atkinson et al. |
| 5,279,596 | A | 1/1994 | Castaneda et al. |
| 5,308,324 | A | 5/1994 | Hammerslag et al. |
| 5,344,395 | A | 9/1994 | Whalen et al. |
| 5,378,234 | A | 1/1995 | Hammerslag et al. |
| 5,387,225 | A | 2/1995 | Euteneuer et al. |
| 5,397,305 | A | 3/1995 | Kawula et al. |
| 5,409,470 | A | 4/1995 | McIntyre et al. |
| 5,423,755 | A | 6/1995 | Kesten et al. |
| 5,458,585 | A * | 10/1995 | Salmon .................... A61B 8/12 600/467 |
| 5,569,197 | A | 10/1996 | Helmus et al. |
| 5,571,073 | A | 11/1996 | Castillo |
| 5,573,520 | A | 11/1996 | Schwartz et al. |
| 5,607,407 | A | 3/1997 | Tolkoff et al. |
| 5,626,593 | A * | 5/1997 | Imran ................. A61B 17/2202 606/159 |
| 5,695,506 | A | 12/1997 | Pike et al. |
| 5,865,767 | A | 2/1999 | Frechette et al. |
| 5,972,019 | A * | 10/1999 | Engelson ............. A61B 17/221 606/159 |
| 5,989,208 | A | 11/1999 | Nita |
| 6,069,965 | A * | 5/2000 | Takewa .................... H04R 9/06 381/403 |
| 6,398,791 | B1 | 6/2002 | Que et al. |
| 6,440,120 | B1 | 8/2002 | Maahs |
| 6,500,147 | B2 | 12/2002 | Omaleki et al. |
| 6,589,253 | B1 | 7/2003 | Cornish et al. |
| 8,034,045 | B1 | 10/2011 | Lyons |
| 2002/0010420 | A1 | 1/2002 | Bagaoisan et al. |
| 2002/0065475 | A1 | 5/2002 | Meguro et al. |
| 2002/0072730 | A1 | 6/2002 | McGill et al. |
| 2003/0018318 | A1 | 1/2003 | Melsky |
| 2003/0028153 | A1 | 2/2003 | Brennan et al. |
| 2003/0191434 | A1 | 10/2003 | Dorros et al. |
| 2004/0030375 | A1 | 2/2004 | Pierce |
| 2005/0245894 | A1 | 11/2005 | Zadno-Azizi |
| 2006/0100602 | A1 | 5/2006 | Klint |
| 2006/0178653 | A1 | 8/2006 | Shimogami et al. |
| 2007/0135830 | A1 | 6/2007 | Schaeffer |
| 2007/0240817 | A1 | 10/2007 | Strong et al. |
| 2007/0260224 | A1 | 11/2007 | Von Oepen et al. |
| 2009/0082723 | A1 | 3/2009 | Krogh et al. |
| 2009/0125043 | A1 * | 5/2009 | Dehnad .............. A61B 17/3207 606/159 |
| 2009/0264910 | A1 | 10/2009 | Laufer |
| 2009/0292296 | A1 | 11/2009 | Pansky et al. |
| 2010/0049167 | A1 | 2/2010 | Myers |
| 2011/0196315 | A1 | 8/2011 | Chappel et al. |
| 2011/0196384 | A1 | 8/2011 | Pansky |
| 2012/0130300 | A1 | 5/2012 | Stavchansky et al. |
| 2012/0165789 | A1 * | 6/2012 | Deckard ................ A61B 17/22 604/528 |
| 2012/0165850 | A1 | 6/2012 | Deckard et al. |
| 2012/0323145 | A1 | 12/2012 | Nagano et al. |

FOREIGN PATENT DOCUMENTS

| | | |
|---|---|---|
| DE | 40 36 570 A1 | 5/1992 |
| EA | 005391 | 2/2005 |
| EP | 0 443 256 A1 | 8/1991 |
| JP | 63-238873 | 10/1988 |
| JP | H05-261114 | 10/1993 |
| JP | H06-23053 | 2/1994 |
| JP | H07-236695 | 9/1995 |
| JP | H08-501945 | 3/1996 |
| JP | 2682831 | 8/1997 |
| JP | 2000-502264 A | 2/2000 |
| JP | 2001-129002 A | 5/2001 |
| JP | 2001-157712 | 6/2001 |
| JP | 2001-204825 | 7/2001 |
| JP | 2002-224221 | 8/2002 |
| JP | 2003-520651 | 7/2003 |
| JP | 2003-521279 | 7/2003 |
| JP | 2005-511108 | 4/2005 |
| JP | 3638304 | 4/2005 |
| JP | 2006-271901 | 10/2006 |
| JP | 2010-022566 A | 2/2010 |
| JP | 2010-513034 A | 4/2010 |
| JP | 2011-078525 | 4/2011 |
| JP | 2011-512956 | 4/2011 |
| JP | 2013-518691 | 5/2013 |
| JP | 2013-518693 | 5/2013 |
| RU | 2207823 | 7/2003 |
| RU | 2302267 C2 | 7/2007 |
| RU | 91674 U1 | 2/2010 |
| WO | WO 93/11711 | 6/1993 |
| WO | WO 96/08196 A1 | 3/1996 |
| WO | WO 97/19644 A1 | 6/1997 |
| WO | WO 01/08737 | 2/2001 |
| WO | WO 01/51114 | 7/2001 |
| WO | WO 2006/042157 | 4/2006 |
| WO | WO 2006/093274 | 9/2006 |
| WO | WO 2009/108816 | 9/2009 |
| WO | WO 2009/141810 A2 | 11/2009 |

OTHER PUBLICATIONS

International Search Report and Written Opinion from corresponding PCT Application No. PCT/IB2014/003282 dated Feb. 5, 2016, 14 pages.
Extended European Search Report from corresponding application EP 18151191.6 dated Apr. 24, 2018, 8 pages.
Russian Search Report from corresponding application RU 2016129731 dated Jan. 18, 2018, 4 pages.

(56) References Cited

OTHER PUBLICATIONS

Russian Search Report from related application No. RU 2016129732 dated Jun. 8, 2018, 4 pages.
International Search Report and Written Opinion from related PCT Application No. PCT/IB2011/000401 dated Jul. 6, 2011, 16 pages.
Russian Search Report from related application No. RU 2014148109 dated Jun. 2, 2016, 4 pages.
Extended European Search Report from related application No. EP 18150461.4 dated Apr. 6, 2018, 9 pages.
International Search Report and Written Opinion from related PCT Application No. PCT/IB2014/000699 dated Nov. 7, 2014, 13 pages.
International Search Report and Written Opinoin from related PCT Application No. PCT/IB2011/000386 dated Jun. 29, 2011, 12 pages.

* cited by examiner

DEVICE FOR TRAVERSING VESSEL OCCLUSIONS AND METHOD OF USE

FIELD OF THE INVENTION

The invention is directed to an energy efficient apparatus and method of using that apparatus for penetrating a total occlusion of a blood vessel during percutaneous coronary intervention (PCI) or improving deliverability of a percutaneous transluminal angioplasty (PTA) catheter through a partial occlusion of a blood vessel. In particular, the apparatus provides efficient energy transfer to the distal end of the device via a pulling force, to penetrate the occlusion with minimal energy loss, as well as a distal end section that combines longitudinal stiffness for effective penetration of occlusions and axial flexibility for deliverability. The apparatus is also applicable to percutaneous intervention procedures in peripheral arteries.

BACKGROUND OF THE INVENTION

Medical science has long sought effective treatments for disease conditions involving stenosis (narrowing or obstruction) of the lumen of an artery. This condition, known generally as an occlusion, occurs in patients suffering from atherosclerosis, which is characterized by an accumulation of fibrous, fatty or calcified tissue in the arteries, otherwise known as atheromata or plaques. An occlusion may be partial or total; it may be soft and pliable or hard and calcified. Occlusions can arise at a great variety of sites in the arterial system including the aorta, the coronary and carotid arteries, and peripheral arteries. An occlusion can result in hypertension, ischemia, angina, myocardial infarction, stroke and even death.

Minimally invasive procedures are the preferred treatment of arterial occlusions. In these procedures, a catheter—a long, highly flexible tubular device—is introduced into a major artery through a small arterial puncture made in the groin, upper arm, upper leg, or neck. The catheter is advanced and steered into the site of the stenosis. A great variety of devices have been developed for treating the stenosed artery, and these devices are placed at the distal end of the catheter and delivered thereby. Example procedures include percutaneous transluminal coronary angioplasty (PTCA), directional coronary atherectomy (DCA), and stenting.

In a total occlusion, a passageway must first be opened through the occlusion to allow the balloon/stent catheter to be placed in the target stenosed segment of the vessel. As occlusion morphology is complicated and varies from patient to patient, common methods and devices for opening these occlusions have had limited success and require long procedures with potentially adverse effects on the patient. Such adverse effects include perforation of blood vessel wall, high radiation dose or damage to kidneys due to extensive use of angiographic contrast material.

Stenoses, or occlusions, are made of a variety of materials—from softer fatty substances such as cholesterol, to tougher fibrous material, to hard calcified material. Generally the ends of the occlusion—the proximal and distal caps—comprise the harder calcified material. The harder materials are more difficult to penetrate, requiring a significant amount of energy, the softer materials require less energy. Therefore, opening an occlusion requires transfer of relatively extensive energy to the distal end of a catheter or guide wire, especially when calcification is present.

Occlusions comprise a variety of materials of different density and hardness. Therefore, the nature of the energy used in a re-canalization device should suit the specific occlusion and the penetration should be controlled to prevent perforation of the artery walls or damage to healthy tissue. Additionally, because the energy originates at the proximal end of the catheter it must be able to reach the distal end of the device near the occlusion at a level sufficient to effect penetration of the occlusion without damaging the conductive wires and without sacrificing flexibility of the device. Current devices suffer either from an insufficient amount of energy transferred to the distal end of the device or a mismatch between the type of energy delivered and the type of occlusion, sometimes resulting in too much force being applied and thereby increasing the risk of damage, or even perforation, of the lumen wall. Accordingly, there is a need for a system or apparatus that can transfer adequate energy to the re-canalization device.

In endolumenal devices designed for penetrating vessel occlusions, mechanical movement, i.e., oscillation, of the member that contacts the occlusion is usually generated by placing an energy source at the proximal end of the device and transferring the energy to the distal end of the device by mechanical means. Some available methods for opening total occlusions are radio-frequency ablative energy (as used in the system sold by Intralumenal Therapeutics as Safe-cross™), vibrational energy of about 20 kHz and small amplitudes (as used in the system sold by FlowCardia Inc. as Crosser™), dedicated stiff guide wire which pushes a passage through the occlusion (as developed by Asahi Intec Co. and distributed as Confianza 9 g/Conquest and Miracle 12 g guide wires) and mechanical vibration elements working at high frequency (FlowCardia Inc.'s Crosser™). All such devices provide limited success rate ranging from 40-70%.

The mechanical vibration means for opening occlusions suffer from significant energy loss between the energy source at the proximal end of the catheter and the driller located at the distal end of the catheter, as well as limited working life due to material fatigue.

With an ultrasound catheter, the ultrasonic energy usually originates from an ultrasound transducer at the proximal end of the catheter and is then transmitted to the distal head of the catheter as a sinusoidal wave, causing the distal head to vibrate and either ablate or disrupt the target occlusion. To reach treatment sites, such catheters must be rather long—about 90-150 cm or more—and therefore a large amount of energy must initially be transmitted to reach the distal end. At the same time, to be flexible enough to course through highly tortuous vessels, the catheter must be reasonably thin. The long length and narrow diameter combine to make wire breakage a common problem due to the stress and wear from the high energy pulses.

Guide wires stiff enough to penetrate hard occlusions have the disadvantage that their inflexibility and straight tips make navigating through tortuous vessels difficult and increase the risk of vessel perforation. Rigid materials that are sufficiently flexible to accommodate the highly tortuous vessels have the problem of buckling, due to the proximal location of the pushing source. Buckling results in energy loss by transfer to transverse forces and friction against the lumen housing the rigid material. For example, one prior art device (i.e., FlowCardia Inc.'s Crosser™) uses a rigid Nitinol wire. The rigidity of the wire permits an axial force initiated at the proximal end of the wire to be transmitted to the distal end of the wire, by pushing the wire. However, such energy transfer mechanisms suffer from significant, yet unpredictable (i.e., variable), energy loss due to energy transfer to the housing tube (e.g., catheter lumen). This is a particular problem when the rigid wire bends to conform to the anatomy of the blood vessel. Energy loss of rigid wires are due mainly to two mechanisms: (1) Moment of inertia, which may be illustrated by bending a rigid body. The force imposed to bend the rigid wire is transferred to friction when the rigid wire is housed within a catheter lumen. (2) Buckling of the wire, a situation that causes the axial force to be shifted to transverse forces and results in increased friction forces within the housing lumen. Further, if the axial force is increased to compensate for the energy losses, the buckling is exacerbated, making axial oscillation, and in particular controllable axial oscillation, even more difficult to achieve.

An important engineering phenomenon is the buckling of slender beams upon load. The critical force required to buckle a slender beam (including, for example, a rigid wire) is given by Equation 1:

$$F_c = \frac{\pi^2 EI}{(KL)^2}, \quad (1)$$

where $F_c$ is maximum force the rigid wire can support without buckling, L is the length of the rigid wire, and K is a numeric constant which depends on the way the rigid wire is supported at its ends. For example, if both ends are pinned (i.e., free to rotate), then K=1. If one end is pinned and the other end is fixed, then K=0.7. If a straight wire that is held at its distal end is pushed at its proximal end by a force exceeding the critical buckling force $F_c$, the rigid wire will buckle laterally, and will not transmit the pushing force ahead.

A rigid wire winding within a catheter lumen—in particular a catheter that courses through a tortuous blood vessel—will be bent. Even without pulling or pushing such a rigid wire, there are forces exerted upon the rigid wire to keep it bent. Friction created by the bent wire against the lumenal surface of the catheter causes the rigid wire to be pinned at some point. If the friction at the pinned point is larger than the buckling threshold, a buckling will occur and adversely affect the pushability of the wire. The resistance that a rigid wire meets at a vessel occlusion works the same way as a pinned point due to friction at a bend. A rigid wire in a tube such as a catheter will move only if the pushing force is larger than the friction force or resistance acting upon the rigid wire. If the length of the straight portion of the rigid wire preceding the point of resistance is long enough, however, the rigid wire will buckle before the pushing force becomes large enough to overcome the friction. This explains why it is difficult to transmit a force to one end of a winding rigid wire by pushing from the opposite end, because the rigid wire is expected to buckle.

Therefore, there is a need in the art for an apparatus for penetrating vessel occlusions that is capable of delivering efficient energy in a controlled and safe manner to open vessel occlusions, and to improve the deliverability of catheters carrying such devices through blood vessels. There is also a need in the art for an energy efficient apparatus for penetrating vessel occlusions that has a leading edge or distal section for vibrating that is sufficiently rigid longitudinally to act as a drilling head to penetrate calcified lesions at the treatment site, but that also has sufficient axial flexibility for deliverability through tortuous vessels and narrow and stenosed vessels. There also is a need for a system that can both transfer adequate energy and adjust the amount of energy transmitted to the penetrating end of the device based on the hardness of the occlusion.

SUMMARY OF THE INVENTION

The invention is directed to an apparatus for re-canalization of a total or partial occlusion in a body lumen, such as a blood vessel. The apparatus of the invention includes a catheter tip with a proximal section that is a spring member and a distal section that is a drilling component, or drilling head. The portion of the apparatus that impacts the occlusion is vibratable; this vibratable member is the drilling component. The spring member has open coils (gaps between the coils) and the drilling component is a coiled wire, or spring, with closed coils (adjacent coils contact each other). For example, the spring member may have at least two neighboring coils with open construction. This novel dual arrangement provides a drilling head at the distal end of the catheter tip that has and combines sufficient longitudinal stiffness for drilling with good axial (lateral) flexibility to improve the deliverability and crossability of the catheter tip and catheter, and a mechanism for oscillating the drilling component that avoids the problem in the art of mechanical energy loss between the external energy source and the distal point of oscillation.

In particular, the apparatus of the invention comprises a spring member, a pulling member, a vibratable drilling component, all housed in a catheter. The drilling component, or drilling head, is located at the distal tip of the apparatus and is made to oscillate in response to the pulling force of the pulling member and the return force of the spring member upon release of the pulling member. The oscillation or vibration of the drilling component can effect penetration of the occlusion.

The drilling component is a tightly coiled (closed coil) spring, i.e., the neighboring coils contact each other. For example, the drilling component may have at least two neighboring coils that are tightly packed. As used herein, the concept of "closed coils" is used interchangeably with "tightly packed coils" and "tightly coiled". The closed coil construction of the drilling component of the invention has the benefit of longitudinal stiffness that can provide pushability, like a solid drilling head, but also flexibility along its axis, which a solid drilling head does not provide. In a preferred embodiment, the coiled drilling component is tapered distally to reduce the crossing profile and enhance deliverability. In one aspect of this embodiment, the drilling component has an external diameter that tapers distally, i.e., the diameter decreases from the proximal end to the distal end, and an inner diameter (lumen diameter) that is constant from the proximal to distal end or tapers at a lesser rate than the outer diameter.

The apparatus of the invention preferably includes a vibrational energy source located external of the catheter and operably connected to the pulling member, which moves freely relative to the catheter. The vibrational energy source is adapted to repeatedly pull and release the pulling member so as to vibrate the drilling component via the spring member.

The apparatus may additionally comprise a device that secures the catheter relative to the blood vessel to improve the delivery of vibration forces to the occlusion. The apparatus may still further comprise a steering device to assist navigation through an occlusion, especially for use in cases where there are numerous bifurcations near the target occlusion. The catheter may be compatible for use with additional external or internal components that assist visualization of the apparatus or device, and/or to remove drilling debris, for example by suction.

The system of the invention comprises the apparatus of the invention, including the vibrational energy source, and a control unit adapted for controlling the vibrational energy source. The vibrational energy source generates a vibration force having at least one frequency and at least one amplitude, and the control unit may independently adjust the frequency and amplitude of vibration in the vibrational energy source and, thereby, of the drilling component. Suitable vibration force may be achieved by adjusting the frequency, e.g., from several Hz to several hundred Hz, and/or adjusting the pulling amplitude, so that the penetration force of the vibration is minimized and is appropriate for the occlusion morphology and hardness. Therefore, the control unit may adjust the vibrational energy source to generate a vibration force suitable for the occlusion morphology and hardness.

It is believed that by providing the minimal force necessary to penetrate an occlusion, safety of the recanalization procedure is increased and potential damage to the body lumen, e.g., an artery, is reduced compared to recanalization devices in the art. Accordingly, the frequency and/or amplitude of vibration of the drilling component may be changed manually by the physician operator to adjust for the hardness of the particular occlusion being treated, based on the operator's skill and experience. Alternatively, the frequency and amplitude of vibration may be adjusted automatically or manually based on measurements of the hardness of the occlusion.

Where the hardness of the occlusion is to be measured, the apparatus of the invention may comprise a sensor or strain gauge. Optionally, the system of the invention further comprises an operator interface unit to assist the operator in controlling the frequency and amplitude of vibration of the drilling component based on feedback from the sensor regarding hardness of the occlusion and/or Δy (expansion) of a compression spring member. The control unit adjusts the frequency and/or amplitude at which the vibrational energy source pulls the pulling member and may be, for example, a switch, a processor, or a processor with an operator interface unit.

The system may further include a tension control mechanism to compensate for variations in the path of the pulling member in curved or tortuous lumens. The tension control mechanism may adjust the length of the pulling member or the amplitude that the pulling member is pulled.

The invention further encompasses a method of oscillating the drilling component, a method of using the apparatus or system for recanalization of an occluded body lumen, such as a blood vessel, and a method of controlling the force of vibration in the apparatus. The result is a versatile and efficient energy delivery apparatus, system and method for penetrating a total occlusion and/or improving deliverability of the catheter through partially occluded body lumens.

It is an object of the invention to provide an improved apparatus for penetrating a vessel occlusion and/or traversing a partial occlusion, where the apparatus has a vibratable member that is made to vibrate in an improved manner, namely, by more efficient energy transfer from the external energy source to the distal part of the catheter. The increased efficiency derives from the pulling wire-spring combination of the apparatus. In particular, the apparatus generates a vibration force that oscillates the vibratable member by a pulling force rather than pushing or combined pulling-pushing force. The apparatus of the invention is less sensitive to unpredictable geometry such as the sometimes tortuous curvature of blood vessels than PCI devices that use pushing forces.

It also is an object of the invention to provide such an energy efficient apparatus that has as the vibratable member a drilling component having the combined properties of flexibility for delivery through difficult vessel anatomies and adequate longitudinal stiffness for drilling through calcified vessel lesions.

It is further an object of the invention to provide such a drilling component that tapers distally.

It is a further object of the invention to provide a system comprising an apparatus with a pulling force for penetrating a vessel occlusion that is capable of adjusting the frequency or amplitude of vibration to accommodate the hardness of the occlusion or stretching of the pulling member.

DESCRIPTION OF DRAWINGS

FIG. 1A depicts an apparatus with no tension placed on it. FIG. 1B depicts the apparatus with tension in the pulling member, and a spring member compressed with load (stored energy). Stored energy is equal to spring constant (k) multiplied by compression amplitude (x). FIG. 1C depicts the apparatus with no tension in the pulling member released, and kinetic energy releasing from the compression spring. FIG. 1D depicts the apparatus with no tension in the pulling member, and the compression spring at maximum expansion ($y_x$) for the compression amplitude (x). FIG. 1E depicts the apparatus with tension on the pulling member again.

DETAILED DESCRIPTION OF THE INVENTION

Figure 1:
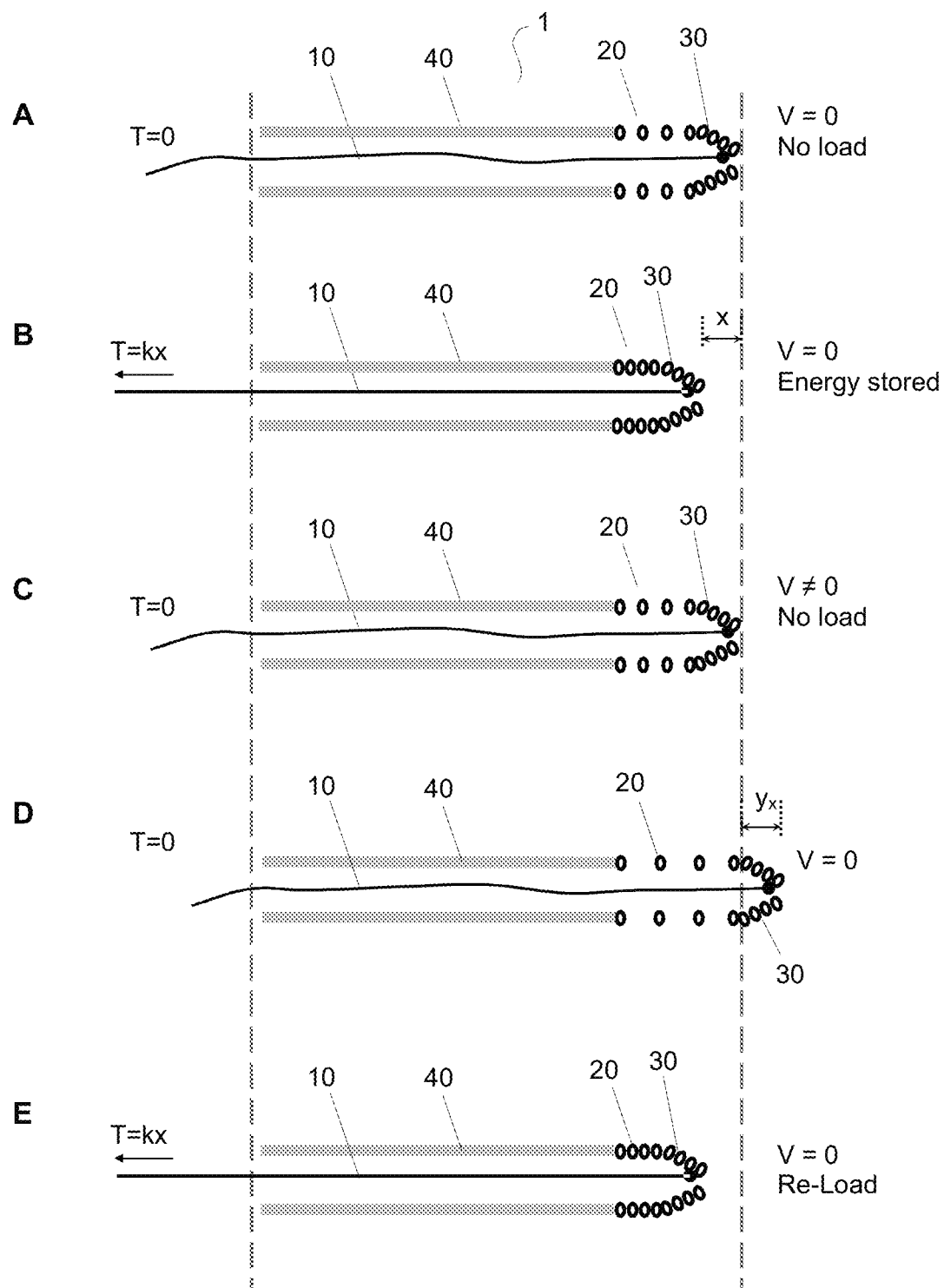
FIGS. 1A-1E illustrate one way an embodiment of the apparatus of invention may work during one pulling cycle.

The apparatus, system and method of the invention provide an improved device and method for oscillating a drilling component to re-canalize a total or partial occlusion in a blood vessel, but may also be applicable to clearing occlusions from other body lumens. The apparatus of the invention includes a spring member and drilling component at the distal end of the catheter, i.e., in the catheter tip, and a pulling member attached to the spring member or drilling component and housed in a catheter. The apparatus provides therapeutic vibration in the drilling component at the distal end of the catheter, i.e., in the catheter tip. The vibratable drilling component is operably affixed to the distal end of the spring member. Vibration of the drilling component is effected via the spring member by pulling and releasing the pulling member.

More particularly, when pulled, the pulling member, which may be attached either to the spring member or to the drilling component, may compress the spring member in the proximal direction and thereby transfer potential energy to the drilling component. Upon release of the pulling member tension, the spring member converts the stored energy to kinetic energy locally, thereby moving the drilling component in the distal direction. The acceleration of the kinetic energy may cause expansion of the spring member to extend the distal end of the spring member beyond the no load (resting) position, thereby pushing the drilling component further distally. In a blood vessel having an occlusion, the kinetic energy is transferred from the drilling component to impact the occlusion. The drilling component, located at the distal-most part of the catheter tip, is thereby made oscillate at a frequency and amplitude sufficient to penetrate an occlusion in a body lumen.

The drilling component comprises a tightly coiled (tightly packed or "closed coil") wire configuration. The tightly coiled wire configuration of the drilling component provides axial flexibility (i.e., the drilling component may flex laterally) as well as longitudinal stiffness or pushability, for example to effect drilling through an occlusion.

The catheter may be a conventional interventional medical catheter having a lumen to accommodate the pulling member and preferably also a lumen to accommodate a guide wire as well as other elements such as for steering, motion measurement element, to infuse contrast material, or to remove occlusion debris from the drilling area.

Thus, the apparatus of the invention comprises a catheter, having a proximal end and a distal end; a spring member having a proximal end and a distal end, said proximal end of said spring member being affixed to said distal end of said catheter, said spring member having at least two neighboring coils with open construction; a drilling component contiguous with said distal end of said spring member and functionally attached thereto, said drilling component comprising a spring having at least two neighboring coils that are tightly packed; and a pulling member housed within said catheter, said pulling member having a proximal end and a distal end, said distal end of said pulling member affixed to a distal structure selected from the group consisting of said spring member and said drilling component; wherein said pulling member, when pulled and released compresses and releases said spring member thereby effecting at least one oscillation of said drilling component. The apparatus may further comprise a vibrational energy source operably connected to said proximal end of said pulling member, wherein said vibrational energy source oscillates said drilling component by repeatedly pulling and releasing said pulling member.

The apparatus may be alternatively described as comprising a catheter having a proximal end, a distal end, and a catheter tip at said distal end of said catheter; a pulling member located within said catheter, said pulling member having a proximal end and a distal end, said distal end of said pulling member affixed to a structure in said catheter tip; and a vibrational energy source operably connected to said proximal end of said pulling member, wherein said vibrational energy source is adapted to generate at least one oscillation in said drilling component via said pulling member and said spring member; wherein said catheter tip comprises a spring member and a drilling component; said spring member having a proximal end and a distal end, said proximal end of said spring member being affixed to said distal end of said catheter, said spring member having open coils; said drilling component having a proximal end and a distal end, said proximal end of said drilling component being connected to said distal end of said spring member, said drilling component consisting of a tightly coiled wire.

In one embodiment, the drilling component tapers distally. In one aspect of this embodiment, the spring member tapers distally. In another embodiment, the drilling component has an outer diameter that tapers distally and an inner luminal diameter that is substantially constant, i.e., constant or near constant. In one aspect of this embodiment, the spring member also has an outer diameter that tapers distally and an inner luminal diameter that is substantially constant, i.e., constant or near constant. In yet another embodiment, the drilling component has an outer diameter that tapers distally at a first rate and an inner luminal diameter that tapers at a second rate, said second rate less than said first rate. In one aspect of this embodiment, the spring member also has an outer diameter that tapers distally at a first rate and an inner luminal diameter that tapers distally at a second rate, said second rate less than said first rate.

In one embodiment the catheter tip structure that the pulling member is attached to is the drilling component. In another embodiment, the spring member is a compression spring, and said pulling member is affixed to said distal end of said spring member. With respect to embodiments in which the pulling member is attached to the spring member, the pulling member may be attached at any point along the spring. For example, the pulling member may be attached proximal of a taper area, distal of a taper area, or at any point between the distal end of the spring member and a point on the spring member distal of the catheter to which it is attached.

The system of the invention comprises the apparatus of the invention, including the vibrational energy source, and a control unit for controlling vibrational energy source. The control unit may also control or adjust independently the at least one frequency and at least one amplitude of the oscillation. The system may further comprise a sensor to assist controlling the frequency or amplitude and a processor functionally connected to said sensor and operably connected to said control unit, the processor capable of analyzing input from the sensor. The control unit may further comprise an operator interface unit (i.e., a user input-output device). The system may still further include a tension control (or adjustment) mechanism to compensate for variations in pulling member path length when the catheter includes curvatures, i.e., is curved due to the curvatures of the vessel.

The invention further provides a method of oscillating a drilling component of a catheter tip and a method of traversing a vessel occlusion using the apparatus, for example to recanalize an occlusion. Also provided is a method of controlling the force of vibration.

The method of oscillating a drilling component of a catheter tip, the catheter tip comprising a compressible spring member having a proximal end and a distal end, said proximal end of said spring member being affixed to said distal end of said catheter; an axially flexible drilling component contiguous with said distal end of said spring member, said drilling component consisting of a tightly packed coil spring; a pulling member housed within said catheter, said pulling member having a proximal end and a distal end, said distal end of said pulling member affixed to a distal structure in the catheter tip. The distal structure may be selected from the group consisting of: said spring member and said drilling component. The method of oscillating a drilling component comprises pulling the pulling member from a proximal end of said pulling member to generate a load that compresses the distal end of the spring member toward the proximal end of said spring member, said pulling member attached at a distal end to said distal end of said spring member, wherein said drilling component is functionally attached to said distal end of said spring element; releasing said load generated by said pulling member, thereby permitting said spring member to expand; repeating said pulling and releasing steps to effect oscillation of said drilling component. When the distal structure to which the pulling member is attached is the spring member, the pulling member may be attached at any point along the spring member that permits generating a load on the spring member by pulling the pulling member. Thus, in another embodiment, said distal end of said pulling member is attached to a point proximal of a taper area of said spring member. In yet another embodiment, said distal end of said pulling member is attached to a point distal of a taper area of said spring member. In each of these alternative embodiments, pulling said pulling member generates a load on said spring member, by compressing said spring member, and releasing said pulling member releases said load to effect oscillation of said drilling component.

In one embodiment, the pulling and releasing is performed by a vibrational energy source. In one aspect of this embodiment the oscillation has at least one frequency and at least one amplitude, and said at least one frequency is controlled by a control unit functionally attached to said vibrational energy source. In another aspect of this embodiment the oscillation has at least one frequency and at least one amplitude, and said at least one amplitude is controlled by a control unit functionally attached to said vibrational energy source. In yet another aspect of this embodiment the oscillation has at least one frequency and at least one amplitude, and said at least one frequency and said at least one amplitude are controlled by a control unit functionally attached to said vibrational energy source.

The method of traversing a catheter through a vessel occlusion comprises introducing into the vessel the apparatus described above; positioning said drilling component in contact with said occlusion; and generating a series of pulling forces from said vibrational energy source upon said pulling member to oscillate said drilling component at an amplitude and frequency sufficient to penetrate said occlusion. The method may further include advancing said catheter through said occlusion as said drilling component penetrates said occlusion. The method may further include in the generating step oscillating said drilling component at an amplitude and frequency sufficient to maneuver said catheter around obstacles in said vessel.

The tightly coiled wire configuration of the drilling component provides improved maneuverability of the catheter tip through, e.g., tortuous vessels compared to a drilling head having a solid, rigid structure. In addition to being axially flexible, the tightly packed coils provide pushability to the drilling component and rigidity at the distal end, in particular at the distal edge. In a preferred embodiment, the drilling component tapers distally. For example, in one aspect of this embodiment, the drilling component may have an external diameter that tapers from the proximal end to the distal end. In this aspect, the lumen of the drilling component may have a constant diameter or may taper distally at a lesser degree than the outer or external diameter. The coils of the drilling component may comprise metal, hard plastic, or other suitable materials. Suitable metal materials for the drilling component include, for example, stainless steel, cobalt chromium, Nitinol or other appropriate metals that would be apparent to one skilled in the art from the description herein.

The spring member may be, for example, a compression spring, a helical spring (e.g., a wire in the shape of a helix), a leaf-spring, a bellows, a compressible polymer, a coated spring, or similar member suitable for storing potential energy upon compression and releasing kinetic energy when the compression load is lifted. The compression and expansion of the spring member may be used to vibrate the drilling component at a frequency and amplitude sufficient to penetrate a vessel occlusion.

The drilling component and spring member may be different sections of a single coiled wire spring, the distal section consisting of closed coils and the proximal section having open coils.

The pulling member preferably is a flexible string. Any high tensile polymer would be suitable material for a pulling member. Non-limiting examples of suitable materials include carbon, DSM Dyneema® or Dyneema Purity® (available from DSM, Heerlen, Netherlands), or other suitable polymers, such as a polyethylene or a polyester.

The vibrational energy source may be any energy source that is capable of generating at least one vibratory energy pulse by pulling and releasing. The vibrational energy source may be, for example, an actuator, a solenoid, a shaker, for example a vibrational shaker, a motor, for example a standard motor or a piezoelectric motor, or any similar energy source having a reciprocating member that can pull and release the pulling member. By "release" is meant releasing the tension in the pulling member, the tension being generated by pulling the pulling member. The vibrational energy source is located external of the catheter. The vibrational energy source pulls the pulling member to generate potential energy in the spring member. The potential energy converts to kinetic energy when tension in the pulling member is released, the load on the spring is lifted and the spring member expands naturally, thereby locally transferring mechanical energy to the drilling component, pushing the drilling component distally, e.g., toward the occlusion. The process is repeated at a frequency and amplitude that enables the drilling component to drill through the occlusion. The amount of energy can be adjusted by choosing an appropriate "spring" member having an internal spring factor (k). The force may be further adjusted by externally setting the pulling member amplitude. The amount of power (energy over time) as well as the mechanical impact can be controlled by the oscillation frequency.

Specifically, the force for generating therapeutic vibration of the drilling component may be provided by the vibrational energy source, which is capable of pulling the pulling member at a distance (x), to generate a tension (T), and then releasing the tension. The pulling member is functionally connected at its distal end to the spring member. The structure in the catheter tip to which the pulling member is attached may be the drilling component or the spring member, for example the distal end of the spring member. A return force is provided by the spring member, having a spring constant (k), such that the tension in the pulling member may be defined as $T=kx$. The repeated combination of pulling and releasing of the pulling member generates oscillations in a drilling component at a frequency and amplitude sufficient to penetrate and clear a vessel occlusion. The operator may adjust the vibration by adjusting the frequency and/or amplitude of vibration through a control unit, which controls the vibrational energy source.

The catheter may have one or more lumens for the pulling member(s) and a lumen for a guide wire. The catheter may also include various lumens for other features, such as a steering wire or other mechanism, contrast materials for visualization, IVUS (intra-vascular ultrasound), elements for measuring distal motion amplitude and force, removal of debris from the occlusion, etc.

The apparatus of the present invention overcomes the limitations of the prior art—in particular the loss of mechanical energy between the proximal end of the device where an energy source may be located and the distal end of the device where the drilling occurs, by providing a distal spring-like element, a spring member, to transmit force locally. The spring member is capable of being charged—e.g., being compressed to generate potential energy—by a flexible pulling member. The potential energy is converted to kinetic energy upon release of tension in the pulling member. The potential energy is loaded and released to kinetic energy at a desired frequency and amplitude to oscillate a drilling component. The stored energy of the spring member is released to the occlusion via the drilling component, which impacts the occlusion. As used herein, the term "flexible" is intended to mean capable of flexing laterally without any inertia moment, e.g., to accommodate tortuous vessels, but not longitudinally—e.g., the pulling member should be minimally stretchable or extensible lengthwise. By "releasing the pulling member" is meant that the tension—generated in the pulling member by pulling the pulling member—is released.

In contrast to the energy lost when transmitting energy from the proximal to distal end of a device, as is typical of prior art devices, energy loss is minimized in the instant invention by use of the spring member and pulling member combination. The apparatus of the invention comprising a pulling and releasing process is more efficient than pushing a stiff wire, even when the path of the pulling member deviates from a straight path, for example when the catheter flexes. The more efficient energy transfer feature of the present invention provides improved penetration of partially or totally occluded vessels as well as improved deliverability of PTA catheters. Accordingly, an advantage of the pulling member feature of the invention is that the force will not significantly diminish in strength from the proximal end of the apparatus where the energy is generated to the distal end of the apparatus, where the drilling component impacts the occlusion. Another major advantage of the invention is that the force is fully controlled by the user (amplitude and frequency), allowing the user to match the force to the occlusion and keep the procedure safe. Various amplitude-force combinations can be achieved by appropriate choice of spring member placed at the distal end of the catheter.

The system of the invention comprises a control unit that is capable of adjusting the force applied against the occlusion by adjusting frequency or by adjusting the amplitude of oscillation of the vibratable member automatically or at the behest of the operator, e.g., a physician. The operator may fine-tune the particular frequency or amplitude of oscillation of the drilling component at any given time directly via the control unit or indirectly through an operator interface unit operably connected to the control unit.

Occlusions, in particular vascular occlusions, tend to have non-uniform density and hardness. Penetrating harder parts of an occlusion requires a relatively larger force than what is necessary for softer parts of the occlusion. The minimal force necessary to recanalize a path through an occlusion is realized by the combination of frequency and amplitude of vibration. Increasing the amplitude of vibration or increasing the frequency of vibration will increase the force. Decreasing the amplitude or frequency of vibration will decrease the force.

Determining the appropriate force for a given occlusion may be done "by feel" by the physician operator, based on the physician's experience and diagnostic skill. The operator may adjust the vibration to provide an appropriate force to penetrate an occlusion, by manually adjusting the frequency and/or amplitude of vibration directly through the control unit. Alternatively, the apparatus of the invention may further comprise a sensor (e.g., a tissue sensor) designed to measure directly or indirectly the hardness or stiffness of the biological matter forming the occlusion, and the amplitude and/or frequency of vibration of the vibratable member may be adjusted based on feedback from the sensor.

The sensor may be, for example, a strain gauge sensor, a piezoresistor, a microstrain sensor, or a magnetic sensor. A strain gauge is a device used to measure deformation (strain) of an object. The most common type of strain gauge consists of an insulating flexible backing which supports a metallic foil pattern. The gauge is attached to the object by a suitable adhesive, such as cyanoacrylate. As the object is deformed, the foil is deformed, causing its electrical resistance to change. This resistance change, usually measured using a Wheatstone bridge, is related to the strain by the quantity known as a gauge factor. Commercial example of such a strain gauge that may be useful in the present invention is the Vishay 015DJ strain gauge (Vishay Intertechnology, Inc., Malvern, Pa., U.S.A.). A piezoresistor is a resistor made from a piezoresistive material having a sensitivity proportional to the piezoresistive gauge factor of the piezoresistor, which is defined by the relative change in resistance with strain. Silicon is a common material with which to form sensors comprising piezoresistors. Such piezoresistor sensors may comprise, for example, four 6-10 µm by 30-50 µm piezoresistors implanted in a high aspect-ratio cross-shape flexible element having a 525 µm high silicon mesa, as described in Beccai, L. et al., "Design and fabrication of a hybrid silicon three-axial force sensor for biomechanical applications," *Sensors and Actuators A: Physical*, Vol. 120, Issue 2, pp. 370-382, May 17, 2005. Piezoresistors are also described in U.S. Pat. Nos. 4,419,598 and 6,441,716, which are incorporated herein by reference; WO 2005/106417 describes strain sensors based on piezoresistor nanowires. Magnetoelastic sensors are low cost, miniature sensors with no moving parts, having other properties expected useful for biological applications. Magnetoelastic sensors are described in U.S. Pat. No. 7,062,981, which is incorporated herein by reference. Commercial examples of such magnetoelastic sensors that may be useful in the present invention are DVRT Microminiature Displacement Sensors (MicroStrain, Inc., Burlington, Vt., U.S.A.).

The sensor may be located at the distal end of the catheter to directly measure the resistance the occlusion impact element encounters against the occlusion. Occlusion hardness also may be determined by measuring how much the spring member expands after the load is released. In one mode of operation for directly measuring expansion of the spring member a magnetic sensor may be located in the catheter, for example attached to the internal catheter wall or changes in the amount of expansion or rate of deceleration upon impact with the occlusion may indirectly measure hardness or stiffness of the occlusion. The expected amplitude of oscillation of the vibratable member (i.e., vibration force amplitude) may set by the operator, and if the spring member expands less than the set amount, the calculated difference provides a measure of how much more pulling force is required to achieve the correct amplitude of oscillation to penetrate the occlusion. In any mode of operation, the sensor may provide feedback to a processor that generates a readable output for the operator who can manually adjust the energy pulse input and subsequent pulling force through a control unit. Alternatively, the sensor may provide feedback directly to the control unit that can be made to adjust the pulling force input automatically.

In one embodiment the system in which the apparatus comprises a sensor, a processor located in either the control unit or user input-output device (also referred to herein as an operator interface unit) may analyze input from the sensor or strain gauge to calculate tissue hardness or amplitude of vibration, and thereby allow the frequency and/or amplitude of vibration to be adjusted automatically by the control unit or manually by the physician operator based on operator-readable output from the operator interface unit. Optionally, the operator interface unit may include a display unit, for example a display screen, for displaying information regarding occlusion hardness or amplitude of vibration in a user-readable form. In embodiments in which the operator adjusts the vibrational energy source, the control unit or operator interface unit may comprise one or more adjustor means for the operator to adjust manually the frequency and/or amplitude of the pulling force generated by the vibrational energy source. The adjustor means may be, for example, knobs, dials, buttons levers and the like that permit adjustment of the amplitude or frequency of the pulling force generated by the vibrational energy source, digitally or in analog, similar to a rheostat or potentiometer.

The system may further include a tension control system. The shape of the catheter changes as it encounters curvatures in the vessel, which changes in the distance through the catheter that the pulling member must traverse. For example, if the catheter is routed through a curved or tortuous lumen, the path that the pulling member takes through the catheter lumen changes, for example tending toward the inside of the curve rather than through the middle of the lumen. This can amount to about a 1% or so difference in distance from the vibrational energy source to the drilling component of the apparatus, thereby affecting the efficiency of pulling the pulling member to effect oscillation at the vibratable member at the distal end of the catheter. A shorter path may result in decreased tension on the pulling member, and a greater pull amplitude by the vibrational energy source may be required to achieve a constant tension. In order to accommodate changes in the pulling member path and control the pulling member tension, in one embodiment the system may include a tension control mechanism that adjusts the length of the pulling member. In this way, the tension of pulling member may be maintained at the desired constant tension, thereby improving efficiency of the apparatus. The tension control mechanism may adjust the length of the pulling member. In a preferred aspect of this embodiment, the length of the pulling member is adjusted in the region between the catheter body and the motor of the vibrational energy source. In an alternative embodiment, the system may include a tension control mechanism that adjusts the amplitude that the pulling member is pulled.

Exemplary embodiments of the invention are described in detail below with reference to the drawings. The drawings, which are schematic and not necessarily to scale, are provided to depict particular aspects of the embodiments and are not intended to limit the scope of the invention.

In the particular embodiment illustrated in FIGS. 1A-E, the spring member 20 is shown as a compression spring. The pulling member 10 is attached, at its distal end, to a drilling component 30, which is attached to the distal end of the spring member 20 (compression spring) and serves as the vibratable member. The spring member 20 is attached at its proximal end to the distal end of the catheter 40. A compression spring is designed to provide resistance to compressive forces. In accordance with the invention, the pulling member 10 is used to compress the spring member 20 (compression spring) at a tension (T), where T=kx, (k) is the spring constant and (x) is the spring deflection (also referred to herein as "compression distance")—ideally, the distance the pulling member 10 is pulled. Upon release of the tension on the pulling member 10, the spring member 20 (compression spring) naturally expands and preferably if no resistance exists the spring member 20 (compression spring) expands further approximately a distance (y) before returning to its unloaded position (0). In cases where the spring member meets resistance, such as an occlusion, the spring will expand to the point it hits the occlusion and may not reach the expansion position attainable in the absence of resistance. In such cases $\Delta y$ will be less than $\Delta y_x$, where $y_x$ is the natural expansion for a spring member compressed by x (deflection=x). The optimal spring constant (k) for such a compression spring in accordance with the invention is between about 0.1-10 Newton per mm.

FIGS. 1A-E illustrate more particularly in transverse section through the catheter tip 1 the status of an embodiment of the apparatus of the invention comprising a spring member that is a compression spring at different points in time during one pulling cycle. In the context of this drawing, "one pulling cycle" means one pull and release of the pulling member. FIG. 1A illustrates the elements of the catheter tip 1 at rest, the pulling member 10 having no tension and spring member 20 bearing no load. As shown in FIG. 1B, when tension (T) is applied to the pulling member 10, the spring member 20 is compressed, thereby storing energy. FIG. 1C illustrates the apparatus at some stage after the pulling member 10 has been released, dropping the tension in the pulling member 10 to zero (T=0). Upon release of the pulling member 10 by the vibrational energy source (not shown), the spring member 20 expands in the axial direction. Expansion of the spring member 20 moves the drilling component distally at a rate greater than 0 (V>0). The rate of mechanical movement (V, velocity) of the cap at the time illustrated in FIG. 1C, where kinetic energy is maximal as the spring member 20 is midway between peak compression and peak expansion for the given applied tension (i.e., equivalent to its resting position), may be expressed as V=2π A sin(2πf·t), where A is the compression amplitude, f is the frequency, and t is time. This velocity excludes forces exerted in the proximal direction by an occlusion. As shown in FIG. 1D, in the absence of external resistance such as a vessel occlusion, the spring member 20 will continue to expand beyond its resting position a distance ($y_x$), which may be approximately equal to (x), where the velocity reaches zero again (V=0) and then naturally compress—providing a return force—towards its resting position (deflection=0). In use, at this point, the vibrational energy source will again pull the pulling member 10 a distance (x), as illustrated at the peak tension (T=kx) in FIG. 1E.

The repeated pulling and releasing of the pulling member results in oscillation of the drilling component, which is attached to the distal end of the spring member. The amplitude of oscillation of the drilling component may be controlled by the distance the pulling member is pulled. The frequency of oscillation will be a function of the rate of pulling and release of the pulling member and the spring constant. The frequency of the pulling/releasing generated by the vibrational energy source preferably is lower than the natural frequency of the spring.

The embodiment illustrated in FIGS. 1A-E shows the pulling member attached to a drilling component, which may also be referred to as the vibratable member of the apparatus. Alternatively, the distal structure of the catheter tip to which said pulling member may be attached is the spring member. The drilling component is the element of the apparatus that, in use, comes into contact with the vessel occlusion and serves as the part of the apparatus that penetrates and drills through the occlusion.

In a preferred embodiment, as illustrated in FIGS. 1A-E, the spring member is a compression spring. The pulling cycles may be effected by a vibrational energy source. The vibrational energy source may mechanically pull the pulling member, the pulling member may cause the spring member to compress, and the drilling component thereby may be made to move proximally. Then, after tension in the pulling member is released, causing the spring member to expand, the drilling component may be made to move distally.

In a preferred embodiment, the spring member has an open coil construction. By "open coil" is meant at least two coils of the spring are spaced apart. For example, 2-10 coils may be spaced apart, or 5-20 coils may be spaced apart. The total number of coils in the spring member will be a function of the length of the spring member, the spaces between the coils, and the cross-sectional diameter of the wire that forms the coil.

Spring members other than compression springs may operate in the same manner in accordance with the invention. For example, the spring member may be a helical spring, a leaf spring, a bellows, or a compressible polymer. Alternatively, where the amplitude of the vibration is desired to be smaller and the frequency and force higher, the pulling member may be attached at a point on the spring member proximal of the distal end of the spring member.

In one embodiment, the spring member is a bellows. As used herein, the bellows is essentially a sealed element which has a return force (spring constant) built into it and may be, for example, a sealed coated spring or corrugated tube comprising a compression spring. The bellows may have an open design or a closed design. By "closed design" for a bellows is meant that one end of the bellows is closed, as a cup; by "open design" for a bellows is meant that both ends of the bellows are open, as a tube. For the closed design, the closed end would be located at the distal end. Thus, where the bellows is a closed design, the bellows is operably connected at its distal closed end to the pulling member. The structures of these bellows may be designed so that they may be contracted upon load from the pulling member and returned (expanded) by the internal spring force upon removal of the external load. Bellows useful in the present invention are available from, for example, MS Bellows, 5322 McFadden Ave, Huntington Beach, Calif. 92649. The terms "bellows" and "spring bellows" are used interchangeably herein. Alternatively, the ordinarily skilled artisan can make a distal bellows by covering a spring with a polymer or embedding a spring in a polymer, such that the polymer membrane is extensible in the longitudinal (axial) direction. Preferably the polymer material has a lower durometer (shore) than the material making up the outer walls of the catheter.

In this embodiment the pulling member may be attached to the distal end of a closed bellows or to the drilling component, which is operably attached to the distal end of the bellows. In this arrangement, similar to the compression spring, when the vibrational energy source exerts a tension on the pulling member, the pulling member causes the bellows to compress, so that the distal end of the bellows is deflected by distance (x). When the vibrational energy source releases the tension on the pulling member, the bellows expands, and the distal end of the bellows is returned to its unloaded position (deflection 0), and preferably moves distally beyond (0) to a deflection of approximately (y) distally, before returning to the unloaded position (0).

According to this embodiment, the bellows are intended to compress upon load from the pulling member and expand upon removal of the load. The repeated loading and unloading of the bellows results in an oscillation of the distal end of the bellows to which is attached the drilling component.

In general, the drilling component 30, 130, 230, 330, 530 may taper distally in order to decrease the crossing profile of the catheter tip. Tapering will result in a decreased entry profile and thereby improve deliverability and crossability through narrowed and/or stenosed vessels and/or calcified lesions. For some applications, it may be preferable that the inner diameter of the tapered drilling component (the lumen diameter) does not itself taper. In such embodiments, the drilling component has an inner diameter (lumen diameter) that is constant along the entire length of the drilling component. In other words, the inner diameter is the same along the axial length of the drilling component, while the outer diameter gradually decreases in the distal direction. Alternatively, the inner diameter of the drilling component may narrow distally, but at a lower rate than the narrowing of the outer diameter, i.e., having less taper than the outer diameter. It is the narrowing (rate of decrease) of the outer diameter that determines the actual extent of tapering of the drilling component. In one embodiment, the spring member also tapers distally, and in a particular aspect of this embodiment the spring member, like the drilling component, has an outer diameter that tapers and an inner luminal diameter that does not taper—i.e., has a constant or near constant diameter.

One advantage in having a drilling component, or catheter tip (spring member and drilling component), with constant or near-constant inner diameter is that this design may control and limit internal friction between the drilling component (or catheter tip) and the guide wire that passes therethrough. Another advantage lies in limiting the friction between the drilling component (or catheter tip) and the mandrel on which the catheter is mounted during manufacturing.

Figure 2:
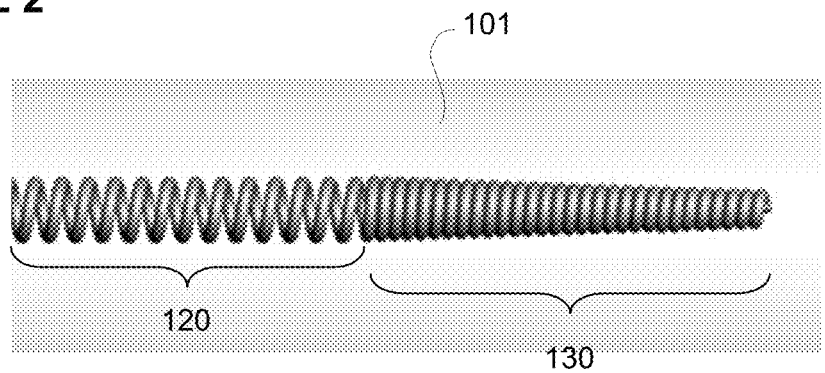
FIG. 2 illustrates a spring member and drilling component of a catheter tip according to the invention.

FIG. 2 illustrates an example of a catheter tip 101 according to the invention comprising a spring member 120 and drilling component 130 for use in the apparatus of the invention. In this embodiment the drilling component is tapered, the outer diameter and inner diameter tapering at the same rate (shown) or at different rates (not shown), and the spring member 120 is not tapered. The embodiment depicted in FIG. 2 also illustrates a single coiled wire spring having a distal section and a proximal section, wherein the distal section is the tightly coiled drilling component 130 and the proximal section is the open coil spring member 120.

Figure 3A:
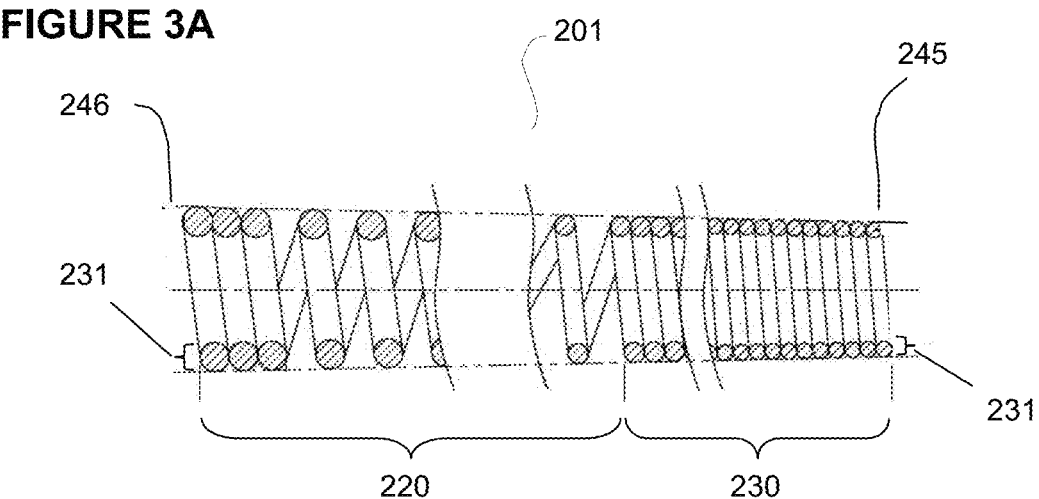
FIG. 3A illustrates a cross-sectional view of an embodiment of a catheter tip according to the invention that is a coil wire with tapered outer diameter and constant luminal diameter, the coil wire including a spring member having spaced coils and a drilling component having tightly spaced coils.
Figure 3B:
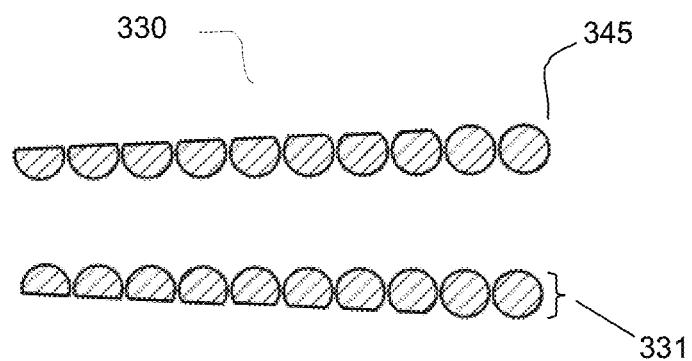
FIG. 3B illustrates a cross-sectional view of an embodiment of a tapered drilling component having a constant luminal diameter.

Exemplary embodiments of tapered drilling components having a constant inner diameter for use in the catheter tips of the invention are illustrated in FIGS. 3A and 3B. The spring member may also taper distally and, as shown in FIG.

3A. In this aspect, the tapered spring member may have an inner luminal diameter that is constant or near constant. In another aspect (not shown) the spring member inner luminal diameter tapers at a lesser rate than the outer diameter.

One method of tapering the outer diameter of the drilling component while maintaining a constant or near constant inner diameter is to manufacture the catheter tip as a coiled wire from a tapered wire. By "tapered wire" is meant a wire having a decreasing cross-sectional diameter 231 along its length. Such a tapered catheter tip comprising a tapered spring member 220 (having spaced coils) and tapered drilling component 230 (tightly coiled) is illustrated in FIG. 3A. In one non-limiting embodiment, the cross-sectional diameter 231 of the wire may be 0.1 mm at a first end (proximal end 246 of the wire coil) and the cross-sectional diameter 231 of the wire may be 0.05 mm at a second end (distal end 245 of the wire coil). Other gradations of wire cross-sectional diameter 231 may be used, depending on the degree of taper desired for the spring member 220 and drilling component 230. For example, the cross-sectional diameter of the tapered wire may decrease from 30-70% between the first end and second end. Obtaining a tapered outer diameter while maintaining a constant inner, luminal diameter for the spring member 220 and drilling component 230 formed from a tapered wire may be ensured during manufacturing by winding the tapered wire on a fixed diameter mandrel. The inner, luminal diameter of the resultant wire coil spring member 220 and drilling component 230 remains constant or near constant, and the effect of the decreasing wire diameter will translate into a reduced outer diameter for the resultant catheter tip 201. Similarly, an inner, luminal diameter having a lesser taper than the outer diameter may be achieved during manufacture by winding the tapered wire on a mandrel having a taper rate less than that of the cross-sectional diameter of the tapered wire.

Optionally, the proximal end of the spring member may include a tightly packed section of coils, as illustrated in FIG. 3A, indicated as region A.

FIG. 3B illustrates another embodiment of a tapered drilling component 330 having a distally tapering outer diameter and a constant or near constant an inner (lumen) diameter. A method for producing the embodiment of FIG. 3B involves starting with a non-tapered drilling component (e.g., a coil having a constant outer diameter along its length), and exposing the outer surface of the drilling component to laser radiation or chemical etching, or any other means of grinding or abrading the outer surface of the wire coil, to produce a gradually reduced cross-sectional diameter 331 of the wire coil toward the distal end 345. The coil of the drilling component 330 is thereby rendered to taper distally on its outer surface, while the inner luminal diameter remains substantially constant. Thus, in one aspect of this embodiment, the starting wire cross-sectional diameter may be, for example, 100 micrometers and may be reduced in the distal direction by between about 30-70% from the proximal end 346 to the distal end 345 of the drilling component 330. After abrading the outer surface of the coils to the desired taper, the drilling component 330 may be polished to effect a smooth surface to minimize damage to vessel walls.

The apparatus and system of the invention are compatible for use with imaging components to assist the operator in determining the location of the distal end of the catheter relative to the target occlusion or vessel walls during operation of the device. Thus, the apparatus or system may further comprise imaging components and an imaging system, for example, IVUS, OCR, Doppler ultrasound or other imaging systems known in the art. The catheter may further comprise one or more lumens for optional components, such as a lumen for visualization or imaging component—for example, IVUS, OCR, Doppler ultrasound, fiber optics, or contrast agents, as well as an auxiliary lumen for housing such useful components as steering components or other therapeutic components. A lumen may be designed to function as a guide wire lumen for insertion of the catheter into the body lumen, and then when the guide wire is not needed, it may be removed and the lumen may be used to deploy a visualization device for use during operation of the apparatus—e.g., penetration and traversal of an occlusion. Alternatively, this lumen can be used for suction of debris away from the drilling area during penetration of the occlusion.

In any one of the embodiments of the invention, the apparatus may optionally include a catheter anchoring element that secures the catheter to the walls of the blood vessel. The catheter anchoring element may be used to stabilize the catheter within the body lumen during operation, so as to prevent substantial movement in response to the vibrational forces and to secure the catheter to the walls of the blood vessel to improve vibration force delivery. The catheter anchoring element may be serviced by an anchoring element lumen. The catheter anchoring element may be, for example, one or more expandable balloons. In such an embodiment, the anchoring element lumen may be an inflation lumen filled with a fluid, preferably a liquid, more preferably a biologically compatible liquid, and used to inflate (expand) the one or more expandable balloons to secure the catheter in the blood vessel. Securing the catheter in this manner will make the vibration forces more effective in treating certain types of occlusions.

Figure 4A:
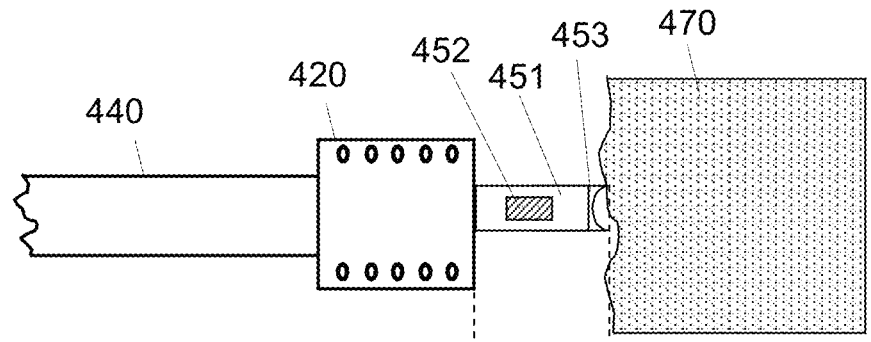
FIGS. 4A-4C are a series of schematic diagrams depicting components of a tissue sensor according to the invention, and illustrating how an embodiment of a tissue sensor attached to a spring member might be used to determine whether the appropriate force is applied to occlusions of differing hardness.
Figure 4B:
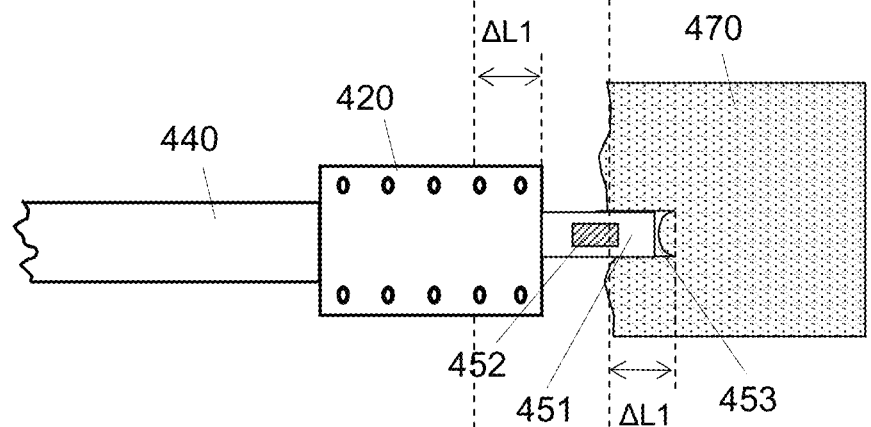
Figure 4C:
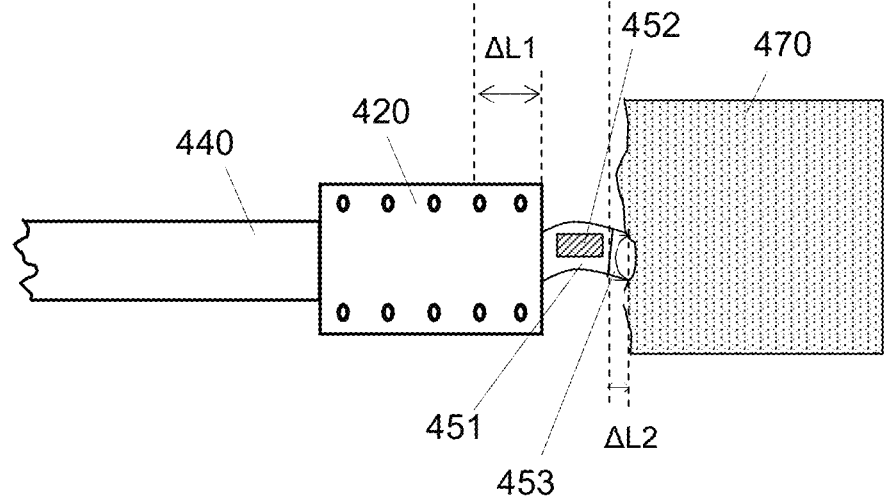

The apparatus of the invention may further comprise a sensor for measuring the hardness of the occlusion to be penetrated. FIGS. 4A-C illustrate aspects of a tissue sensor and its operation with respect to the invention. In particular, FIGS. 4A-C illustrate one way to measure whether desired amplitude is achieved, using a tissue sensor comprising a probe, strain gauge and touch sensor. For clarity of illustration, the drilling component at the distal end of the spring member 420 is not shown in FIGS. 4A-C.

The system may be set by the operator to achieve desired displacement, or target penetration amplitude ($A_0$). The target amplitude, $A_0$, may not be achieved, however, if the applied force does not match the occlusion hardness, and the achieved amplitude (A) must be determined. The achieved amplitude, A, may be monitored via a sensor in any one of several ways described below or that will become apparent to the person of ordinary skill in the art in view of the examples set forth below. For example, achieved amplitude, A, may be measured directly, for example using a strain gauge or by measuring displacement of the distal end of the spring member 420. In such embodiments, the sensor may comprise a probe 451, strain gauge 452, and touch sensor 453, which, as depicted in FIGS. 4A-C, measure occlusion hardness separate from stress on the drilling component. Alternatively, the sensor may comprise a magnetic sensor 560 that may be attached directly to the drilling component 530, as depicted for example in FIGS. 5A-B to measure the amplitude of vibration of the drilling component 530. As the apparatus comprises a spring member 520 that is compressed by pulling the pulling member 510 and upon release expands to exceed its resting position to an extension state, penetration amplitude may be determined by measuring the actual extension distance (achieved amplitude, A, affected by resistance generated by the occlusion) and comparing the expected extension distance of the spring member 520.

The force required to penetrate an occlusion may be estimated using Eq. 2:

$$F = ES\left(\frac{\Delta L}{L_0}\right), \quad (2)$$

where F is the force applied to the object, E is Young's Modulus (hardness or stiffness) of the occlusion, S is the original cross-sectional area through which the force is applied (i.e., the cross-sectional area of the probe or sensor), $\Delta L$ is the amount by which the length of the object changes, and $L_0$ is the original length of the object. To define the mechanical properties of the occlusion tissue, so as to adjust the frequency and amplitude for penetration, two parameters should be monitored: force (F) and displacement (L). Of the other parameters of Eq. 2, S—the cross-sectional area of the probe or sensor (which may be a guide wire or other element with known dimensions)—is known, whereas L—the length of occlusion—is unknown. Nevertheless, the force required to penetrate a tissue of unknown hardness may be determined, as illustrated in FIGS. 4A-C. A catheter 440, a spring member 420 attached to the distal end of the catheter 440, and sensor is provided. The sensor comprises a probe 451, a strain gauge 452, and a touch sensor 453. There are two modes in the working cycle, the measurement mode and the vibration mode. First in the sequence is the measurement, second in the sequence is vibration. In measurement mode, when the touch sensor 453 is placed close to the occlusion 470 and touches it, as shown in FIG. 4A (a contact the physician-operator can feel), the measurement mode is switched on. Measurement mode is a single pulse mode, and the probe may penetrate into the occlusion.

As force (F) is a function of mass (m) and acceleration ($a_{peak}$), an applied force in vibration may be defined as set forth in Eq. 4:

$$F = ma_{peak} = m4\pi^2 \Delta L f^2 \quad (3)$$

Thus, in accordance with Eq. 3, the amount of force to apply is determined by displacement $\Delta L$ and frequency f. Fixing $\Delta L$ (stroke or amplitude of vibration, equivalent to the movement of the distal end of the spring) at a specific target value, for example, 0.1 mm (a value determined from a safety standpoint), force F may be changed by varying the frequency f. At the starting point, the force pulse is provided at a defined frequency f and amplitude A. FIG. 4B illustrates an applied force that is sufficient to penetrate the occlusion at the full depth $\Delta L$. That the target displacement as been achieved may be confirmed with a magnetic sensor, which may provide signals proportional to bending or strain of the probe. See FIGS. 5A-B. In some cases, the pulling member may be made of material that stretches slightly when a critical pulling force is exceeded. Practically, the catheter is unlikely to be completely straight, but rather may be curved or undulating due to the shape of the body lumen, especially in blood vessels. This means that the initial pulling force provided by the vibrational energy source may be absorbed in the pulling member to some extent and cannot be taken at face value for an estimation of occlusion hardness or target amplitude, $A_0$. Moreover, the operator may push the catheter with unknown force, which cannot be controlled or readily measured by the apparatus. In such circumstances, not only the occlusion length but also the actual applied force at the distal end is approximate. Nevertheless, under such conditions, estimation of occlusion tissue mechanical characteristics may be made in relative rather than absolute terms, i.e., values at the distal end can be calibrated from the values at the proximal end. If the initial inputted vibration force is $F_0$ with stroke (amplitude) $\Delta L_0$ at the proximal point, it will reach values $F_1$ and $\Delta L_1$ at the distal point. Thus, if the applied force is sufficient to penetrate into the occlusion tissue 470, the penetration depth will be almost the same as stroke value $\Delta L_1$ or amplitude as shown on FIG. 4B. By contrast, if the applied force is insufficient for full penetration, the probe 451 may bend, as illustrated in FIG. 4C, and the strain gauge sensor 452 may provide a corresponding signal. In this scenario, the applied force may be increased by changing its frequency (frequency-dependent vibration mechanism) or its amplitude (amplitude-dependent vibration mechanism).

Figure 5A:
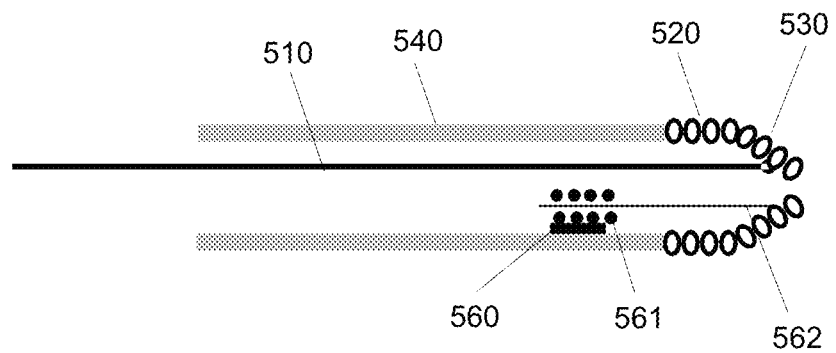
FIGS. 5A-5B illustrate schematically how an embodiment of a sensor might be used to measure directly the achieved amplitude of vibration of the drilling component as the pulling member is pulled FIG. 5A and released FIG. 5B (no load).
Figure 5B:
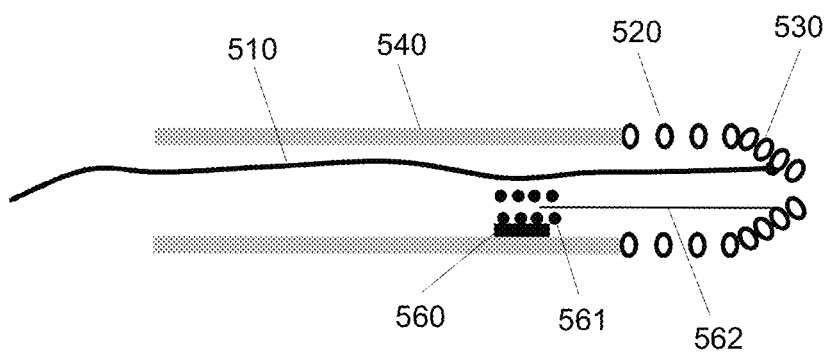

FIGS. 5A and 5B illustrate a sensor for directly measuring the amplitude of vibration of the drilling component. A magnetic sensor 560 may be attached to the internal catheter 540 wall, or to the internal wall of a sensor lumen within the catheter (not shown), and operably connected to the drilling component 530 via a magnetic rod 562. The magnetic rod 562 is movable with the oscillation of the drilling component 530 by pulling and releasing of the pulling member 510. FIG. 5A depicts the position of the magnetic rod 562 relative to the magnetic sensor 560 when the pulling member 510 has been pulled to compress a spring member 520. FIG. 5B depicts the position of the magnetic rod 562 relative to the magnetic sensor 560 when the pulling member 510 when the spring member 520 is at no load. The amplitude of vibration of the drilling component 530 is thereby measureable using the magnetic sensor 560. Alternatively, the magnetic rod 562 may be connected directly to the distal end of the spring member 520 (embodiment not shown). In either embodiment, the magnetic sensor 560 measures directly the achieved amplitude at the distal end of the catheter 540. The achieved amplitude may be less than the target amplitude due to, for example, the resistance encountered by impacting the occlusion. The magnetic sensor 560 depicted in FIGS. 5A-B is a linear variable differential transformer (LVDT) and shows the magnetic rod 562 moveable within the coils 561 of the LVDT, however other magnetic sensors may also be used for direct measurement of achieved amplitude of vibration in accordance with the invention.

Figure 6:
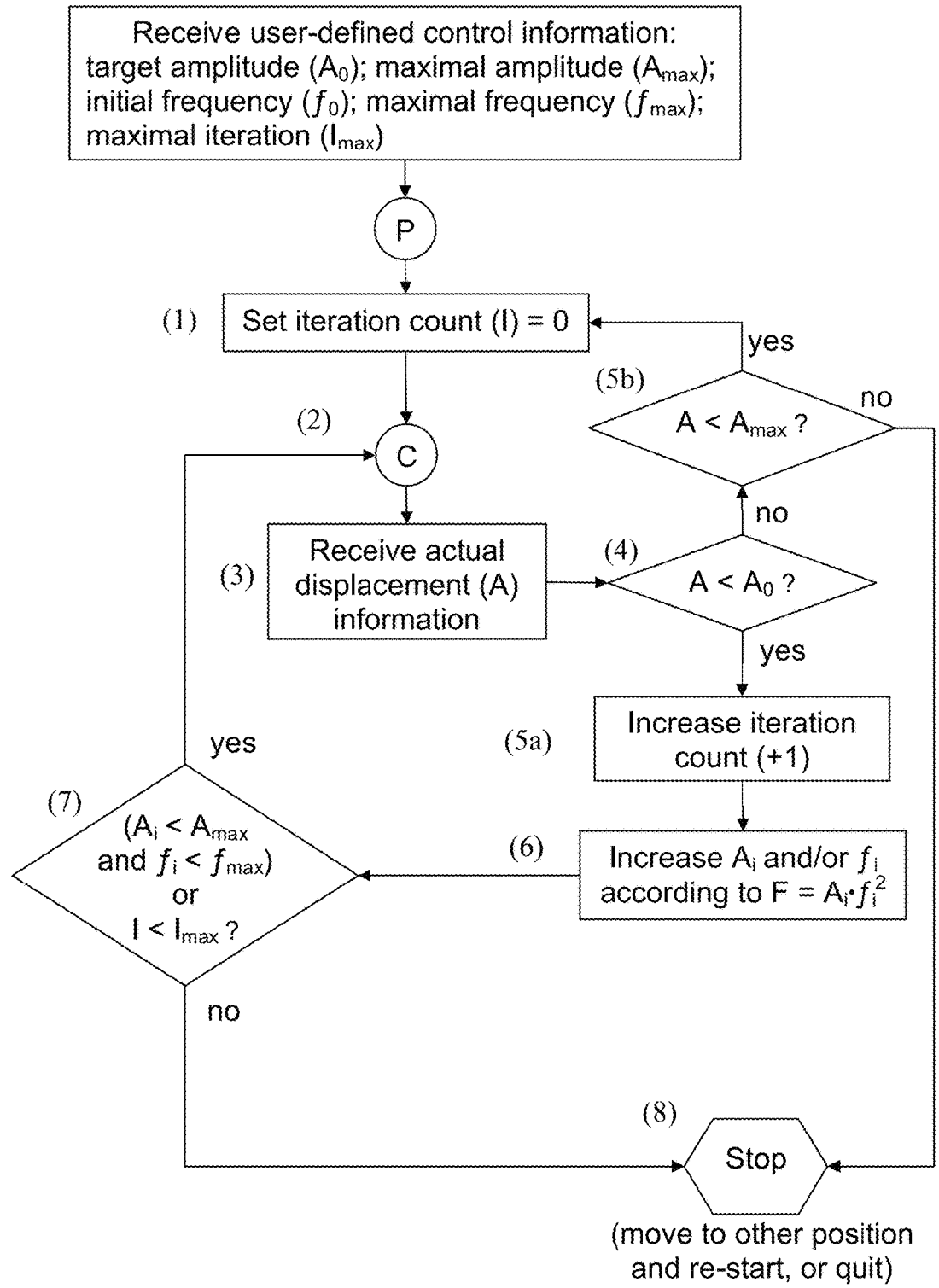
FIG. 6 illustrates one embodiment of a control scheme for adjusting the force of vibration.

The invention encompasses a method of controlling the vibration force. FIG. 6 illustrates one way a control unit might be used in accordance with the invention to monitor penetration amplitude and adjust the amplitude of oscillation if necessary. Control of the frequency and amplitude of vibration is best understood in the context of penetrating an occlusion, such as a vascular occlusion. When the system of the invention is used to penetrate a vessel occlusion, complete penetration may occur over a series of penetration cycles in which frequency and a target amplitude are set prior to initiating vibration in the apparatus, and then adjusted by the control unit throughout the penetration cycle. Each penetration cycle may involve a series of vibration "cycles", in which the effectiveness of the vibration is periodically measured, and the force adjusted as necessary in a manner to maximize both safety and success of penetration. As discussed above, in one mode of operation, the desired penetration amplitude (stroke) may be set at a fixed distance. The control unit of the system of the invention may be used to monitor whether this target penetration amplitude is achieved and to adjust the amplitude and/or frequency of vibration to increase the vibration force accordingly, based on Eq. 4:

$$F = A \cdot f^2 \quad (4)$$

Thus, in such a mode of operation, at the beginning of a penetration cycle, the apparatus may be placed at a first surface of an occlusion, and series of vibration cycles (C) is initiated wherein the control unit controls the force of vibration in response to information from the sensor by adjusting the frequency and/or amplitude of vibration. Once the first surface is penetrated, the apparatus may be advanced to a new face or surface of the occlusion, and a new penetration cycle may be commenced. In this way, the surface of the occlusion may be penetrated in a step-by-step fashion.

Preferably, a penetration cycle (P) begins after initializing the control unit with control information—values relating to amplitude, frequency and vibration adjustment iterations. The control information may be built into the control unit or may be set by the operator. In the embodiment depicted in FIG. 6, the control unit receives the control information from the operator, who sets the initial (target) displacement or amplitude ($A_0$), a maximal displacement ($A_{max}$)—taking into account safety considerations, an initial frequency ($f_0$)—based on assessment of the plaque density, a maximal frequency ($f_{max}$), and a maximal iteration ($I_{max}$). The target amplitude may be, for example, between about 20 μm and about 200 μm. The maximum amplitude may be determined by the operator, for example, based on the lumen diameter and other factors familiar to the skilled artisan. The initial frequency ($f_0$) and maximum frequency ($f_{max}$) may be determined by the operator based on, for example, the particular occlusion to be penetrated and the physical limits of the apparatus or system being used. The control unit preferably has an iteration counter for counting iterations in which the vibration force is changed. The iteration count (I) is not a measure of the number of vibration cycles (V), rather the iteration count is increased only when frequency and/or amplitude are increased. Thus, a vibration cycle (C) may or may not include an adjustment of frequency and/or amplitude, depending on the achieved amplitude (see below). A maximum iteration value ($I_{max}$) may provide either a safety measure (as it may reflect increase in vibration force, as shown below) or a means for an operator to periodically assess the success of the penetration cycle and make adjustments to the procedure as necessary, or both. The series of vibration cycles (C) in the penetration cycle (P) preferably are continuous until the penetration cycle is stopped either by the control unit or the operator. Thus, as used herein, "beginning" or "initiating" a vibration cycle (C) is meant the point in the series of vibrations after the achieved amplitude is compared to the control information. A vibration cycle (C) may be based on units of time or the number of vibrations. Specifically, a vibration cycle (C) can be a predetermined length of time (e.g., 5 seconds or 10 seconds) or a predetermined number of vibration peaks (frequency×time, e.g., number of times the occlusion impact element contacts the occlusion face).

In accordance with the control scheme embodiment illustrated in FIG. 6, after receiving the control information, the control unit sets the iteration count (I) at zero (Step 1). The vibrational energy source is made to generate a pulling force on the pulling member, and a vibration cycle (C) is begun (Step 2). The pulling force having a working amplitude ($A_i$) is expected to generate a distal displacement beyond the resting position of the spring. Distal displacement, or achieved amplitude (A), is measured, preferably via the sensor, and periodically transmitted to be received by the control unit (Step 3), which compares the achieved amplitude (A) to the target amplitude ($A_0$) (Step 4). If the achieved amplitude (A) is less than target amplitude ($A_0$), then an iteration count (I) is added (Step 5a), i.e., I+1, and the working amplitude ($A_i$) and/or working frequency ($f_i$) increased (Step 6) to increase vibration force, in accordance with Eq. 5:

$$F = A_i \cdot f_i^2 \tag{5}$$

where subscript "i" reflects the current iteration count. The force of the oscillated system is proportional to the square of the frequency and amplitude, as shown in Eq. 4 and 5. It is believed that, from a clinical perspective it is better to work at low amplitude, preferably in the range of up to approximately 100 μm (0.1 mm). Thus, to maintain safety of the occlusion penetration procedure, is preferable to increase force by increasing frequency, however the physical structure of the apparatus may impose upper limits on the frequency. So to achieve adequate force for penetration of an occlusion, either frequency or amplitude may be increased up to the maximum values set in the control information. The gain of the amplitude and/or frequency may be increased by about 2% to about 5% each iteration. Thus, for a given total increase in force in a penetration cycle, the number of iteration counts may depend on the percent gain used.

After the vibration force is increased, the iteration count (I) is compared to the maximum iteration value ($I_{max}$), and the working amplitude ($A_i$) and working frequency ($f_i$) are compared to maximum amplitude ($A_{max}$) and maximum frequency ($f_{max}$), respectively (Step 7). If the iteration count (I) is less than the maximum iteration value ($I_{max}$), or if the working amplitude ($A_i$) is less than the maximum amplitude ($A_{max}$) and the working frequency ($f_i$) is less than the maximum frequency ($f_{max}$), the next vibration cycle (C) is initiated (Step 2) at the new working amplitude, new working frequency and new iteration count; the achieved amplitude (A) is again received (Step 3) and compared to the initial (target) displacement ($A_0$) (Step 4), and the cycle continues. However, if after increasing the force, the iteration count (I) is not less than the maximum iteration value ($I_{max}$), and the working amplitude ($A_i$) is not less than the maximum amplitude ($A_{max}$) or the working frequency ($f_i$) is not less than the maximum frequency ($f_{max}$), then the vibration cycle (C) and penetration cycle (P) are stopped (Step 8), and the apparatus may be repositioned within the lumen and a new penetration cycle commenced, or the occlusion penetration is ended.

If, after comparing the measured displacement (achieved amplitude, A) to target amplitude ($A_0$) (Step 4), the achieved amplitude (A) is not less than the target amplitude ($A_0$), then the achieved amplitude (A) is compared to the maximum amplitude ($A_{max}$) (Step 5b). If the achieved amplitude (A) is less than the maximum amplitude ($A_{max}$), the iteration count (I) set to zero (Step 1), and a new vibration cycle is initiated (Step 2) at the same working frequency ($f_i$) and working amplitude ($A_i$), etc. However, if the achieved amplitude (A) is not less than the target amplitude ($A_0$) (Step 4) and also is not less than the maximum amplitude ($A_{max}$) (Step 5b), the vibration cycle (C) and penetration cycle (P) are stopped (Step 8), and the apparatus may be repositioned within the lumen and a new penetration cycle commenced, or the occlusion penetration is ended.

Thus, a method of controlling the frequency and amplitude vibration, and hence the force of vibration, of the apparatus of the invention is provided. In one embodiment, the method for controlling a force of vibration is based on the scheme depicted in FIG. 6. Thus, one method of controlling a force of vibration comprises: a) receiving initial control parameters; b) initiating a vibration iteration cycle comprising at least one pull and release of a pulling member by a vibrational energy source sufficient to vibrate a drilling component at a vibration force (F), wherein said pulling member is attached to a drilling component located at a distal end of a spring member and at a proximal end to said vibration energy source, wherein said spring member is attached at a proximal end to a distal end of a catheter, said catheter houses said pulling member, and said drilling component is attached to said distal end of said spring member, and wherein said pull and release of said pulling member effects a compression and expansion of said spring member; c) receiving an achieved amplitude value input for said vibration iteration cycle; and d) adjusting said vibration force in accordance with said achieved amplitude value. In one aspect, said receiving initial control parameters includes (i) receiving a target amplitude value input; ii) receiving a maximum amplitude value input; iii) receiving an initial frequency value input; iv) receiving a maximum frequency value input; and v) receiving a maximum iteration value input. In another aspect said initiating includes (i) initializing an iteration count to zero; and (ii) commencing said vibration iteration cycle in said apparatus, wherein said at least one pull and release occurs at an initial frequency and a target amplitude. In yet another aspect said adjusting includes (i) comparing said achieved amplitude value to a target amplitude value and to a maximum amplitude value; (ii) increasing an iteration count by one when said achieved amplitude value is less than said target amplitude value, setting said iteration count to zero when said achieved amplitude value is not less than said target amplitude value, and stopping said vibration iteration cycle when said achieved amplitude value is not less than said target amplitude value and not less than said maximum amplitude value; and (iii) increasing said force of vibration by increasing a frequency gain and/or an amplitude gain by about 2-5% in accordance with the equation $F=A_i \times f_i^2$ to generate a new working frequency ($f_i$) and/or a new working amplitude ($A_i$) if said iteration count is increased by one. In a further aspect, said method includes e) comparing said iteration count to a maximum iteration value, comparing said working amplitude to a maximum amplitude value, and comparing said working frequency to a maximum frequency value; f) initiating a new vibration iteration cycle in said apparatus: if said iteration count is less than said iteration maximum value, or if said working amplitude is less than said maximum amplitude value and said working frequency is less than said maximum frequency value; and g) stopping said vibration iteration cycle: if said iteration count is not less than said iteration maximum value, and if said working amplitude is not less than said maximum amplitude value or said working frequency is not less than said maximum frequency value. The method also is applicable where the pulling member is attached to the spring member.

Another method of controlling a force of vibration comprises: a) receiving initial control parameters; b) initiating a vibration iteration cycle comprising at least one pull and release of a pulling member sufficient to vibrate a drilling component at a vibration force (F); c) receiving an achieved amplitude value input for said vibration iteration cycle; and d) adjusting said vibration force in accordance with said achieved amplitude value. The step of receiving control information may further include: (i) receiving a target amplitude value input; ii) receiving a maximum amplitude value input; iii) receiving an initial frequency value input; iv) receiving a maximum frequency value input; and v) receiving a maximum iteration value input. The step of initiating a vibration cycle may further include: (i) initializing an iteration count to zero; and (ii) commencing said vibration iteration cycle in said apparatus, wherein said at least one pull and release occurs at an initial frequency and a target amplitude. The step of adjusting said vibration force may further include: (i) comparing said achieved amplitude value to a target amplitude value and to a maximum amplitude value; (ii) increasing said iteration count by one when said achieved amplitude value is less than said target amplitude value, setting said iteration count to zero when said achieved amplitude value is not less than said target amplitude value, and stopping said vibration iteration cycle when said achieved amplitude value is not less than said target amplitude value and not less than said maximum amplitude value; and (iii) increasing said force of vibration by increasing a frequency gain and/or an amplitude gain by 2-5% in accordance with the equation $F=A_i \times f_i^2$ to generate a new working frequency ($f_i$) and/or a new working amplitude ($A_i$) if said iteration count is increased by one. This embodiment of the method of controlling a force of vibration may further comprise: e) comparing said iteration count to a maximum iteration value, comparing said working amplitude to a maximum amplitude value, and comparing said working frequency to a maximum frequency value; f) initiating a new vibration iteration cycle in said apparatus: if said iteration count is less than said iteration maximum value, or if said working amplitude is less than said maximum amplitude value and said working frequency is less than said maximum frequency value; and g) stopping said vibration iteration cycle: if said iteration count is not less than said iteration maximum value, and if said working amplitude is not less than said maximum amplitude value or said working frequency is not less than said maximum frequency value.

In another embodiment, the method comprises: a) receiving a target amplitude value input, a maximum amplitude value input, a target frequency value input, a maximum frequency value input, and a maximum iteration count input; b) initializing an iteration count to zero; c) initiating a vibration iteration cycle comprising at least one pull and release of a pulling member sufficient to vibrate a drilling component for an iteration at a force of vibration (F); d) receiving an achieved amplitude value input for said vibration iteration cycle; e) comparing said achieved amplitude value to said target amplitude value; f) increasing said iteration count by one and increasing said force of vibration by increasing a frequency gain and/or an amplitude gain by 2-5% in accordance with the equation $F=A_i \times f_i^2$ to generate a working frequency ($f_i$) and/or an working amplitude ($A_i$) if said achieved amplitude value is less than said target amplitude value, and then proceeding to step (j); g) comparing said achieved amplitude value to said maximum amplitude value if said achieved amplitude value is not less than said target amplitude value; h) initializing said iteration count to zero if said achieved amplitude value is less than said maximum amplitude value, and recommencing method at step (c); i) proceeding to step (m) if said achieved amplitude value is not less than said maximum amplitude value; j) comparing said iteration count to said maximum iteration count, comparing said working amplitude to said maximum amplitude value and comparing said working frequency to said maximum frequency value; k) recommencing method at step (c): if said iteration count is less than said maximum iteration count, or if said working amplitude is less than said maximum amplitude value and said working frequency is less than said maximum frequency value; l) proceeding to step (m): if said iteration count is not less than said maximum iteration count, and if either said working amplitude is not less than said maximum amplitude value or said working frequency is not less than said maximum frequency value; and m) stopping said vibration iteration cycle.

The above-described embodiment is only exemplary and is not intended to limit the ways in which a control unit might operate. Any number of control schemes for adjusting the frequency and/or amplitude of vibration may be used. Other methods for control unit operation should be within the skill in the art in view of the disclosure herein. For example, a control scheme may include reducing the vibration force by decreasing the working amplitude when the achieved amplitude is not less than the target amplitude and not less than the maximum amplitude for one or more iterations, before stopping the vibration cycle and penetration cycle.

As described above, there are several ways to monitor the achieved amplitude (A). It can be done using a tissue sensor to measure occlusion hardness or degree of occlusion penetration or using a magnetic sensor to measure displacement of the distal end of the spring member. Preferably, the occlusion penetration procedure begins at a minimal force, which is gradually increased according to the hardness of the tissue. A control algorithm also may be used to calculate the force required based on the feedback regarding occlusion hardness.

In view of the method of adjusting a force of vibration, the method of traversing a vessel occlusion may further include the step of adjusting the frequency and/or amplitude of vibration via a control unit based on occlusion hardness using an embodiment of the above method of controlling force of vibration. Preferably, where the vibration frequency is adjusted to achieve an appropriate force based on information regarding occlusion hardness or displacement of the distal end of the spring member, the device includes a sensor and the occlusion hardness and spring displacement is determined from information from the sensor. In some embodiments, the adjusting step may be performed manually, in other embodiments the adjusting step may be performed automatically. In particular, the method may comprise treating a chronic total occlusion in a blood vessel.

Thus, the invention encompasses in one embodiment, a method of traversing an occlusion in a body lumen, comprising: (a) introducing into said body lumen having said occlusion a catheter comprising a spring member, a drilling component, and a pulling member; wherein said spring member has proximal end and a distal end, said spring member attached at its proximal end to a distal end of said catheter and attached at its distal end to said drilling component; and wherein said pulling member has proximal end and a distal end, said pulling member attached at its distal end to a drilling component located at said distal end of said spring member, and operably connected at its proximal end to a vibrational energy source, said vibrational energy source capable of pulling and releasing said pulling member; (b) advancing said catheter until said drilling component contacts a first face of said occlusion; (c) generating a series of pull and release units via said vibrational energy source sufficient to vibrate said drilling component, wherein said series of pull and release units comprises at least one frequency and at least one amplitude; and (d) using said vibrations of said drilling component to penetrate said first face of said occlusion. In another embodiment, the method further comprises: (e) stopping said vibration; (f) advancing said catheter to contact a new face of said occlusion; (g) repeating steps (a)-(d) until said new face of said occlusion is penetrated; and (h) repeating steps (a)-(g) until said occlusion is completely penetrated.

The method may further comprise the step of adjusting said at least one frequency and/or said at least one amplitude of vibration via a control unit based on occlusion hardness. In one aspect, said catheter includes a sensor and said occlusion hardness is determined from information from said sensor. In another embodiment the method further comprises the step of adjusting said at least one frequency and/or said at least one amplitude of vibration via a control unit based amplitude of vibration of said drilling component. In one aspect, said catheter includes a sensor and said amplitude of vibration is determined from information from said sensor. In a further aspect of any of the above embodiments, said adjusting is done manually. In another further aspect of any of the above embodiments said adjusting is done automatically. In one aspect, said body lumen is a blood vessel.

As is evident by the descriptions above, the apparatus and system are compatible for use with guide wires, which are useful for guiding a catheter through a body lumen, in particular for guiding a catheter through a blood vessel. Stiff guide wires are used in the art for recanalizing blood vessel occlusion. In some cases, physicians prefer to use a stiff guide wire to penetrate a vascular occlusion but demand additional means to effect penetration where the occlusion is particularly difficult and perhaps safety is a concern. The apparatus and system of the invention provide that additional means; the apparatus and system of the invention are compatible with using a stiff guide wire in addition to the pull wire/spring member system to penetrate blood vessel occlusions, including total chronic occlusions. Accordingly, the invention encompasses a method of treating a chronic total occlusion in a body lumen by supplementing the method of penetrating an occlusion described above with using the tip of a guide wire to penetrate the occlusion. Thus, in one aspect of the method of treating an occlusion, said catheter includes a stiff guide wire, and said method further comprises advancing said stiff guide wire to penetrate said face of said occlusion alternately with steps (c)-(d). In another aspect, the method of treating an occlusion further comprises advancing said stiff guide wire to penetrate said face of said occlusion alternately with (c) generating a plurality of pulling and releasing cycles via said vibrational energy source sufficient to vibrate a drilling component, wherein said plurality of pulling and releasing cycles comprises at least one frequency and at least one amplitude, and said drilling component is located at a distal end of said spring member; and (d) using said vibrations of said drilling component to penetrate said first face of said occlusion.

It will be appreciated by persons having ordinary skill in the art that many variations, additions, modifications, and other applications may be made to what has been particularly shown and described herein by way of embodiments, without departing from the spirit or scope of the invention. Therefore it is intended that scope of the invention, as defined by the claims below, includes all foreseeable variations, additions, modifications or applications.

What is claimed is:
1. An apparatus, comprising:
a catheter having a proximal end and a distal end;
a spring member having a proximal end and a distal end, said proximal end of said spring member being affixed to said distal end of said catheter, said spring member comprises a compression spring;
a drilling component contiguous with said distal end of said spring member and functionally attached thereto, said drilling component comprising a spring having at least two tightly packed neighboring coils disposed at a distal-most end of the drilling component; and a pulling member housed within said catheter, said pulling member having a proximal end and a distal end, said distal end of said pulling member affixed to a distal structure selected from the group consisting of said spring member and said drilling component.

2. The apparatus of claim 1, wherein said pulling member, when pulled and released compresses and releases said spring member thereby effecting at least one oscillation of said drilling component.

3. The apparatus of claim 1 or 2, wherein said pulling member is attached to said drilling component.

4. The apparatus of claim 1 or 2, wherein said pulling member is attached to said spring member.

5. The apparatus of claim 1 or 2, wherein said pulling member is affixed to said distal end of said spring member.

6. The apparatus of claim 1 or 2, wherein said spring member is selected from the group consisting of: a helical spring, a leaf spring, a bellows, and a compressible polymer, and said pulling member is affixed to said distal end of said spring member.

7. The apparatus according to claim 1 or 2, further comprising a catheter anchoring device.

8. The apparatus of claim 1, wherein said drilling component is permanently affixed to said spring member.

9. The apparatus of claim 1, wherein the pulling member is a flexible string.

10. The apparatus of claim 9, wherein the string comprises a high tensile polymer.

11. The apparatus of claim 9, wherein the string is a material selected from the group consisting of: carbon, polyethylene, polyester, and ultra-high molecular weight polyethylene.

12. The apparatus of claim 1, wherein said drilling component tapers distally.

13. The apparatus of claim 12, wherein said spring member tapers distally.

14. The apparatus of claim 12, wherein said drilling component has an outer diameter that tapers distally at a first rate and an inner luminal diameter that tapers distally at a second rate, said second rate less than said first rate.

15. The apparatus of claim 12, wherein the drilling component has a proximal end and a distal end, said drilling component tapers to a distal edge of said distal end of said drilling component.

16. The apparatus of claim 12, wherein said drilling component has an outer diameter that tapers distally and an inner luminal diameter that is constant or near constant.

17. The apparatus of claim 16 or 14, wherein said spring member has an outer diameter that tapers distally and an inner luminal diameter that is constant.

18. The apparatus of claim 16 or 14, wherein said spring member has an outer diameter that tapers distally at a first rate and an inner luminal diameter that tapers distally at a second rate, said second rate less than said first rate.

19. The apparatus of claim 1 or 2, further comprising a vibrational energy source operably connected to said proximal end of said pulling member, wherein said vibrational energy source oscillates said drilling component by repeatedly pulling and releasing said pulling member.

20. The apparatus of claim 19, wherein said vibrational energy source is selected from the group consisting of: an engine having a reciprocating member, a shaker, an actuator, and a solenoid.

21. The apparatus of claim 19, wherein the vibrational energy source is located external of said catheter.

22. A method of traversing a catheter through a vessel occlusion comprising: introducing into said vessel the apparatus of claim 19; positioning said drilling component in contact with said occlusion; and generating a series of pulling forces from said vibrational energy source upon said pulling member thereby oscillating said drilling component at an amplitude and frequency sufficient to penetrate said occlusion.

23. The method of claim 22, further including advancing said catheter through said occlusion as said drilling component penetrates said occlusion.

24. The method of claim 22, wherein said generating step includes oscillating said drilling component at an amplitude and frequency sufficient to maneuver said catheter around obstacles in said vessel.

25. A catheter system, comprising:
a catheter having a proximal end, a distal end, and a lumen;
a guidewire extending through the lumen;
a spring member having a proximal end and a distal end, said proximal end of said spring member being affixed to said distal end of said catheter, said spring member comprises a compression spring;
a drilling component contiguous with said distal end of said spring member and functionally attached thereto, said drilling component comprising a spring having at least two tightly packed neighboring coils disposed at a distal-most end of the drilling component; and
a pulling member housed within said catheter, said pulling member having a proximal end and a distal end, said distal end of said pulling member affixed to a distal structure selected from the group consisting of said spring member and said drilling component.

26. The catheter system of claim 25, said lumen is a first lumen, said catheter having a second lumen, wherein the pulling member extends through the second lumen.

* * * * *